United States Patent
Dalton et al.

(12)

(10) Patent No.: US 6,387,885 B1
(45) Date of Patent: May 14, 2002

(54) 3',3'-N-BIS-DESMETHYL-3'-N-CYCLOALKYL ERYTHROMYCIN DERIVATIVES AS LHRH ANTAGONISTS

(75) Inventors: Christopher R. Dalton, Mundelein; Milan Bruncko, Lake Bluff; Michele A. Kaminski, Beach Park; Lisa M. Frey, Mundelein, all of IL (US); Daryl R. Sauer, Trevor, WI (US); Fortuna Haviv, Deerfield, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/140,157

(22) Filed: Aug. 26, 1998

(51) Int. Cl.[7] ................. A61K 31/70; C07H 1/00; C07H 17/08
(52) U.S. Cl. ................ 514/29; 536/7.2; 536/7.4; 536/18.5
(58) Field of Search ............... 536/7.2, 7.5, 18.5; 514/29

(56) References Cited

U.S. PATENT DOCUMENTS 4,677,097 A  6/1987  Omura et al. ............... 514/29

FOREIGN PATENT DOCUMENTS

| EP | 0215355 | 3/1987 |
| EP | 0248279 | 12/1987 |
| EP | 0349100 | 1/1990 |
| EP | 0559896 | 9/1993 |

OTHER PUBLICATIONS

Chem. Pharm. Bull. vol. 37. No. 10 (1989) pp. 2701–2709 T. Sunazuka et al.

*Primary Examiner*—Elli Peselev
(74) *Attorney, Agent, or Firm*—Dugal S. Sickert

(57) ABSTRACT

Disclosed are 3',3'-N-bis-desmethyl-3'-N-cycloalkyl-6-O-methyl-11-deoxy-11,12-cyclic carbamate erythromycin A derivatives which are antagonists of lutenizing hormone-releasing hormone (LHRH). Also disclosed are pharmaceutical compositions comprising the compounds, to methods of using the compounds and to the process of making the same.

13 Claims, No Drawings

3',3'-N-BIS-DESMETHYL-3'-N-CYCLOALKYL ERYTHROMYCIN DERIVATIVES AS LHRH ANTAGONISTS

TECHNICAL FIELD

The present invention relates to a class of macrolide compounds which are antagonists of lutenizing hormone-releasing hormone (LHRH), to pharmaceutical compositions comprising the compounds, to methods of using the compounds and to the process of making the same. More particularly, the present invention relates to 3',3'-N-bis-desmethyl-3'-N-cycloalkyl-6-O-methyl-11-deoxy-11,12-cyclic carbamate erythromycin A derivatives which are antagonists of LHRH.

BACKGROUND OF THE INVENTION

The gonadotropins, follicle stimulating hormone (FSH), lutenizing hormone (LH), and chorionic gonadotropin (CG) are required for ovulation, spermatogenesis, and the biosynthesis of sex steroids. A single hypothalamic hormone, gonadotropin-releasing hormone GnRH also known as LHRH is responsible for regulating the secretion of both FSH and LH in mammals.

LHRH is a decapeptide having the structure:
pyro-Glu$^1$-His$^2$-Trp$^3$-Ser$^4$-Tyr$^5$-Gly$^6$-Leu$^7$-Arg$^8$-Pro$^9$-Gly$^{10}$-NH$_2$
where the superscripts designate the position of each aminoacyl residue in the decapeptide chain.

LHRH is released from the hypothalamus and binds to a receptor on the pituitary gland, causing the release of LH and FSH which subsequently act on the gonads to stimulate the synthesis of steroid sex hormones. The pulsatile release of LHRH, and thereby the release of LH and FSH, controls the reproductive cycle in animals and man. Acute doses of LHRH agonists increase the levels of LH and steroidal sex hormones in both animals and humans. Paradoxically, chronic doses of LHRH agonists suppress the level of LH and steroidal sex hormones. Consequently, the effect of multiple doses of LHRH agonists is to suppress estrogen formation in females and testosterone production in males. The same effect is observed in both animals and humans after administration of either acute or chronic doses of LHRH antagonists.

In recent years considerable research effort has been expended on finding antagonists of LHRH. These efforts have produced a number of peptide LHRH antagonists, which suppress LH and reproductive hormones in mammals upon administration. See for example, M. J. Karten in "Modes of Action of GnRH and GnRH analogs", edited by W. F. Crowley and P. M. Conn, p. 277 (1992). The literature has reported that LHRH antagonists are useful in the treatment of a variety of conditions in which the suppression of sex steroids plays a key role including contraception, delay of puberty, treatment of benign prostatic hyperplasia, palliative treatment or remission of hormonal-dependent tumors of the prostate, the treatment of cryptorchidism, hirustism in women, gastric motility disorders, dysmenorrhea, and endometriosis.

Current LHRH antagonists are decapeptides which, because of their low oral bioavailability, are administered either intravenously or subcutaneously. Non-peptide heterocyclic antagonists have been reported in the literature, see for example, WO 95/280405, WO 95/29900, WO 97/22707, WO 97/21704 and WO 97/2103. Non-peptide LHRH antagonists have the possible advantage of improved oral bioavailability and are smaller molecules.

However, there are no known reports of macrolide compounds as LHRH antagonists in the literature. Macrolide antibiotics and macrolide prokinetic agents are known. For example, macrolide antibiotics derived from erythromycin which contain 11,12-cyclic carbamate moieties are disclosed in EP 248 279 A2. The 3'-N substituted erythromycin derivatives, which are effective antibacterial agents are described in EP 0 559 896 A1. Macrocyclic lactone (macrolide) prokinetic agents are known. See J. S. Gidda et al., in European Patent Application No. 0349100, published Jan. 3, 1990, which discloses 12-membered macrolides for use as gastrointestinal motility enhancers. S. Omura and Z. Itoh, in U.S. Pat. No. 4,677,097, issued Jun. 30, 1987; European Application No. 215,355, published Mar. 25, 1987; and European Application No. 213,617, published Mar. 11, 1987, disclose derivatives of erythromycins A, B, C and D which are useful as stimulants of digestive tract contractile motion. Additionally, T. Sunazuka, et al., Chem. Pharm. Bull. 37(10): 2701–2709 (1989) discloses quaternary derivatives of 8,9-anhydroerythromycin A 6,9-hemiacetal and 9,9-dihydro-erythromycin A 6,9-epoxide with gastrointestinal motor stimulating activity.

None of these references disclose novel 3', 3'-N-bis-desmethyl-3'-N-cycloalkyl-6-O-methyl-11-deoxy-11,12-cyclic carbamate erythromycin A derivatives of the present invention, which are effective as LHRH antagonists.

SUMMARY OF THE INVENTION

In one aspect, the present invention relates to a compound having the formula:

I

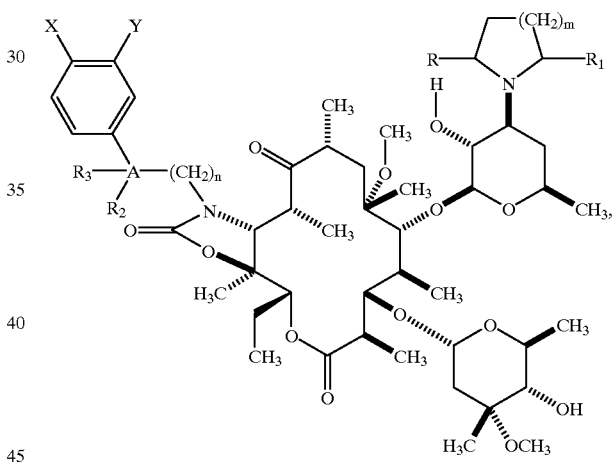

or a pharmaceutically acceptable salt or ester thereof, wherein

A is selected from the group consisting of:
(a) —C,
(b) —N, and
(c) —O;

X and Y are independently at each occurrence selected from the group consisting of:
(a) hydrogen,
(b) halide,
(c) alkoxy,
(d) alkyl,
(e) aryl, and
(f) substituted aryl;

R and R$_1$ are independently selected at each occurrence from the group consisting of:
(a) alkyl,
(b) cycloalkyl,
(c) heterocylic,
(d) substituted heterocyclic,
(e) alkylcycloalkyl, (f) substituted alkylcycloalkyl,
(g) alkylaryl,
(f) alkylheterocyclic,
(g) alkenyl,
(h) alkynyl, m is 1, 2 or 3

$R_2$ and $R_3$ are independently at each occurrence
(a) hydrogen,
(b) methyl, or $R_2$ and $R_3$ together form a cycloalkyl moiety, when A is C; and n=1, 2 or 3.

In another aspect, the present invention relates to a process for preparing the compound formula I. The process comprises the steps of:

(a) reacting a compound of formula:

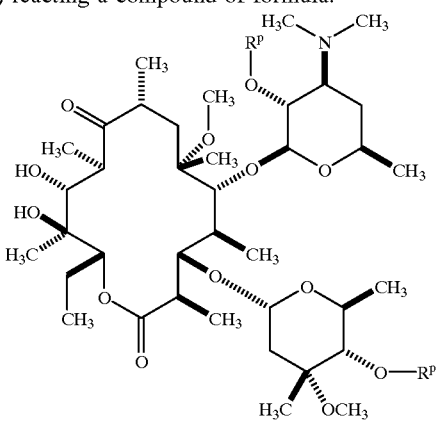

with sodium hexamethyldisilazide and carbonyldiimidazole to afford a compound of the formula:

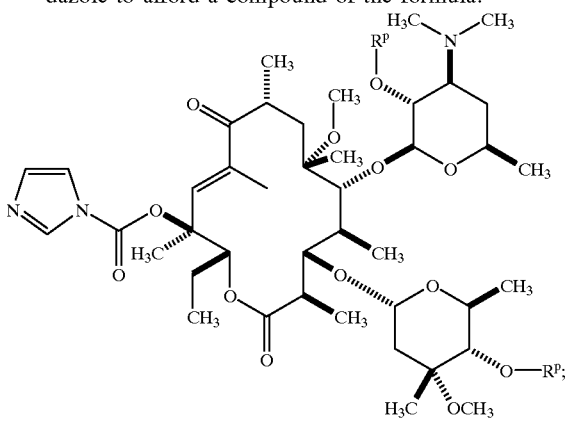

(b) reacting the compound obtained in step (a) with an amino compound of the formula:

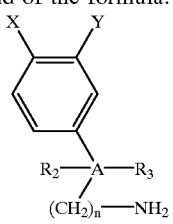

and deprotection to afford a compound of the formula:

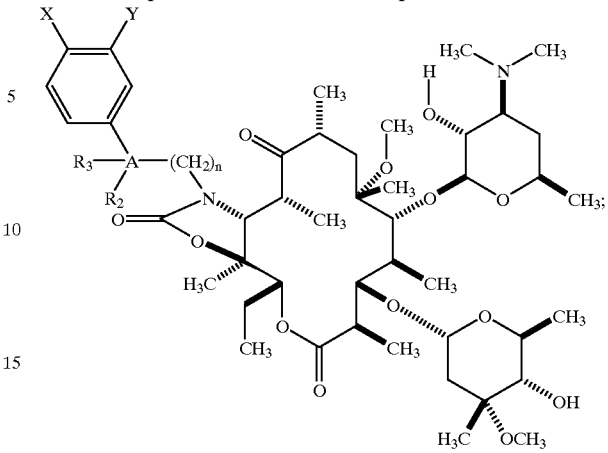

c) stepwise bisdesmethylating the 3'-amino by treating the compound obtained in step (b) twice with iodine in presence of a base to afford a compound of the formula:

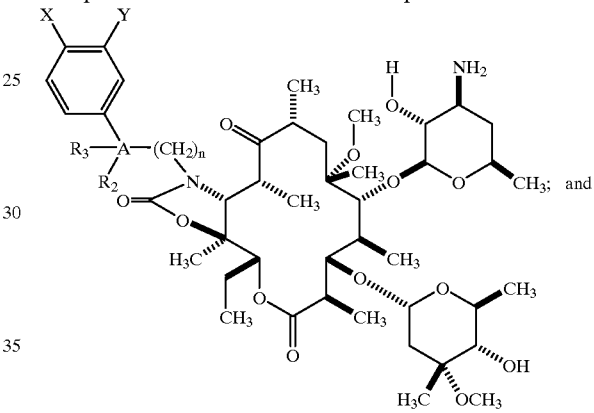

and (d) alkylating the 3',3'-N-bisdesmethylated compound obtained in step (c) with an alkylating agent.

The compounds of the invention exhibit little or no antibacterial activity, but they bind to the LHRH receptors and are effective LHRH antagonists. Thus, these compounds are effective in the treatment of prostate cancer, endometriosis, precocious puberty and other types of diseases which are related to sex hormones.

Accordingly, in another aspect of the invention, the present invention relates to pharmaceutical compositions which are useful as LHRH antagonists and suppress LH and testosterone and estrogen in mammals.

In still another aspect, the present invention relates to a method of suppressing levels of sex hormones in male or female mammals comprising administering to a host in need of such treatment a therapeutically effective amount of an LHRH compounds in combination with a therapeutically effective amount of an antiandrogenic agent.

DETAILED DESCRIPTION OF THE INVENTION

The terms "loweralkyl" or "alkyl" as used herein refer to straight or branched chain alkyl radicals containing from 1 to 20 carbon atoms, sometimes represented as Cx–Cy-alkyl where x and y respectively represent the minimum and maximum number of carbon atoms in the alkyl radical. Examples of loweralkyl include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" or "lower alkoxy" as used herein refers to a loweralkyl group, as defined above, which is bonded to an oxygen atom in an ether linkage. Examples of alkoxy include, but are not limited to, methoxy, ethoxy, isopropoxy, n-pentyloxy, t-butoxy, n-octyloxy and the like. This alkoxy radical can also contain a ring which include, but are not limited to, five or six atom ring composed of carbons, one or two heteroatoms such as nitrogen, oxygen.

The term "alkenyl" as used herein refers to a branched or straight hydrocarbon chain comprising two to twenty carbon atoms, preferably four to twelve carbon atoms, especially about eight to ten carbon atoms, which also comprises one or more carbon—carbon double bonds, preferably about one to three double bonds. Compounds of the invention may either have a known configuration or may exist as a mixture of isomers.

The term "alkynyl" as used herein refers to a branched or straight straight hydrocarbon chain comprising two to twenty carbon atoms, preferably four to twelve carbon atoms, especially about eight to ten carbon atoms, which also comprises one or more carbon—carbon triple bonds, preferably about one triple bond. Compounds of the invention may either have a known configuration or may exist as a mixture of isomers.

The term "cycloalkyl" as used herein refers to a saturated monocyclic hydrocarbon groups having from three to seven carbon atoms in the ring, including, but not limited to, cyclopropyl, cyclobutyl, cyclopentyl, cyclohexyl, cycloheptyl and the like. The cyclic group may be optionally substituted with, for example, lower alkyl, hydroxy, halogen or an amino.

The term "alkylcycloalkyl" as used herein refers to a cycloalkyl group as defined above, appended to a loweralkyl radical. The alkylcycloalkyl group is attached to the parent moiety through the alkyl radical wherein the alkyl radical is of one to six carbon atoms. Examples include, but are not limited to, cyclopropylmethyl, cyclopropylethyl, cyclobutylmethyl and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indenyl, indenyl and the like.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-)amino, formyl, carboxy, alkoxycarbonyl, $C_1$-$C_3$-alkyl-CO—O—, $C_1$-$C_3$-alkyl-CO—NH—, or carboxamide; except that tetrafluorophenyl and pentafluorophenyl are also included within the definition of "substituted aryl".

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, and the like). Heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, piperazinyl, piperidinyl, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (R*N= wherein R* is a loweralkyl group), cycloalkyl, aryl, arylalkyl, and loweralkyl. In addition, nitrogen containing heterocycles can be N-protected.

The term "(heterocyclic)alkyl" as used herein refers to a heterocyclic group as defined above appended to a loweralkyl radical as defined above. The (heterocylic)alkyl group is attached to the parent moiety through an alkyl group wherein the alkyl group is of one to six carbon atoms.

The term "substituted (heterocyclic)alkyl" as used herein, refers to a heterocycloalkyl group, as defined above, wherein the heterocyclic group or the alkyl group is substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, hydroxyalkyl, methoxymethoxy, amino, $C_1$-$C_3$-alkyl-amino, di($C_1$-$C_3$-alkyl-)amino, carboxaldehydo, carboxy, alkoxycarbonyl, $C_1$-$C_3$-alkyl-CO—O—, $C_1$-$C_3$-alkyl—CO—NH—, or carboxamide.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "substituted heteroaryl" as used herein refers to a heteroaryl group as defined herein substituted by independent replacement of one, two or three of the hydrogen atoms thereon with Cl, Br, F, I, OH, $C_1$-$C_3$-alkyl, $C_1$-$C_6$-alkoxy, methoxymethoxy, amino, or $C_1$-$C_3$-alkyl-amino, or may also refer to a mono-oxo substituted heteroaryl compound, such as 4-oxo-1H-quinoline, for example.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methyl-pyrrolidinone, ethers such as diethyl ether and bis-methoxymethyl ether, as well as various other compounds like dimethyl formamide, acetonitrile, acetone and ethyl acetate. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

PREFERRED EMBODIMENTS

The preferred compounds of the invention comprise those in which R, and $R_1$ are independently an alkyl, cycloalkyl, and heterocyclic; X and Y are independently chloro, fluoro, dioxalano, hydrogen, or alkoxy; A is —C; $R_2$ and $R_3$ are both hydrogen; m is 1 or 2 and n is 1.

Representative compounds of the invention are selected from the group consisting of:

3'-Desamino-(3'S)-N-pyrrolidinyl-11-deoxy-11-[carboxy-(3,4-dichlorophenethylamino)]-6-O-methyl-erythromycin A 11,12-(cyclic carbamate);

3'-Desamino-3'-N-pyrrolidinyl-11-deoxy-11-[carboxy-(3-chloro-4-fluorophenethylamino)]-6-O-methyl-erythromycin A 11,12-(cyclic carbamate);

3'-Desamino-3'-N-piperidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3-chloro-4-fluorophenethylamino)]-6-O-methyl-erythromycin A 11,12-(cyclic carbamate);

3'-Desamino-3'S-N-(2,5-dimethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-dimethylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,6-dimethylpiperidinyl)-11-deoxy-11-[carboxy-(3,4-dichlorophenethylamino)]-6-O-methyl-erythromycin A 11,12-(cyclic carbamate);

3'-Desamino-3'-N-(2,6-dimethylpiperidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diethylpyrrolidinyl)-11-deoxy-11-[carboxy-(3,4-dichlorophenethylamnino)]-6-O-methyl-erythromycin A 11,12-(cyclic carbamate);

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate); and 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diallylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diallylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-dipropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-dipropylpyrrolidinyl)-11-deoxy-11-[carboxy-(3,4-dichlorophenethylamnino)]-6-O-methyl-erythromycin A 11,12-(cyclic carbamate);

3'-Desamino-3'-N-(2,5-diisopropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diisopropylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-biscyclopropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-biscyclopropylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-biscyclobutylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-biscyclobutylpyrrolidinyl)-11-deoxy-11-[carboxy-(3,4-dichlorophenethylamino)]-6-O-methyl-erythromycin A 11,12-(cyclic carbamate);

3'-Desamino-3'-N-[2,5-bis(cyclopropylmethyl) pyrrolidinyl]-11-deoxy-11-[carboxy-(3-chloro-4-fluorophenethylamino)]-6-O-methyl-erythromycin A 11,12-(cyclic carbamate); and 3'-Desamino-3'-N-[2,5-bis(cyclopropylmethyl) pyrrolidinyl]-11-deoxy-11-[carboxy-(3,4-dichlorophenethylamino)]-6-O-methyl-erythromycin A 11,12-(cyclic carbamate)

The more preferred compounds are selected from the group consisting of:

3'-Desamino-(3'S)-N-pyrrolidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3-chloro-4-fluorophenethylamino)]-6-O-methyl-erythromycin A 11,12-(cyclic carbamate);

3'-Desamino-3'S-N-(2,5-dimethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-dimethylpyrrolidinyl)-11-deoxy-11-[carboxy-(3-chloro,4-fluorophenethylamino)]-6-O-methyl-erythromycin A 11,12-(cyclic carbamate);

3'-Desamino-3'-N-(2,6-dimethylpiperidinyl)-11-deoxy-11-[carboxy-(3,4-dichlorophenethylamino)]-6-O-methyl-erythromycin A 11,12-(cyclic carbamate);

3'-Desamino-3'-N-(2,6-dimethylpiperidinyl)-11-deoxy-11-[carboxy-(3-chloro, 4-fluorophenethylamino)]-6-O-methyl-erythromycin A 11,12-(cyclic carbamate);

3'-Desamino-3'-N-(2,5-diethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate); and 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate).

Effect and Utilities of LHRH Agonists and Antagonists

The LHRH agonist and antagonist compounds of the invention are useful for treatment of precocious puberty, prostate cancer, benign prostatic hyperplasia (BPH), endometriosis, uterine fibroids, breast cancer, acne, premenstrual syndrome, polycystic ovary syndrome and diseases which result from excesses or deficiencies in gonadal hormone production in either sex of humans and animals. The LHRH antagonists of the invention are also useful for controlling reproduction in both female and males. Compounds of the invention are useful for suppressing levels of testosterone and dihydrotestosterone (DHT) in male and estrogen and estradiol in female.

In the practice of the method of this invention an effective amount of a compound of the invention or a pharmaceutical composition containing the same is administered to the human or animal in need of, or desiring, such treatment. The compound or composition may be administered by any variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male and female mammals for the uses herein above described, it is expedient to administer the active ingredient in amounts between about 1 and 200 mg/kg body weight per day, preferably between 1 and 30 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of afflication or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a poly valent metal cation such as zinc, calcium, bismuth, barium, magnesium, aluminum, copper, cobalt, nickel, cadmium and the like, or with an organic cation formed from e.g., N,N'-debenzylethylenediamine or ethylenediamine; or (c) combinations of (a) and (b) e.g., a zinc tannate salt. Additionally, the compounds of the present invention or preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

LHRH Antagonist Activity

Representative compounds of the present invention were evaluated in in vitro tests for LHRH rat pituitary receptor binding ($pK_I$). The tests employed the methods detailed in F. Haviv, et al. *J. Med. Chem.*, 32: 2340–2344 (1989). The receptor binding affinity ($pK_I$) is the negative logarithms of the equilibrium dissociation constants. The results of the $pK_I$ for representative compounds of this invention are presented in Table 1.

TABLE 1

| Example | $pK_I$ | Example | $pK_I$ |
| --- | --- | --- | --- |
| 1 | 8.74 | 7 | 8.59 |
| 3 | 8.45 | 8 | 8.61 |
| 4 | 8.25 | 9 | 8.76 |
| 5 | 8.91 | 10 | 9.17 |
| 6 | 9.12 | 11 | 8.93 |

Synthetic Methods

The compounds and processes of the present invention will be better understood in connection with the following synthetic Schemes 1 and 2 which illustrate the methods by which the compounds of the invention may be prepared. The compounds are prepared by utilizing commercially available or synthesized reagents.

Abbreviations

Abbreviations which have been used in the descriptions of the scheme and the examples that follow are: Ac for acetyl; APCI for atmospheric pressure chemical ionization; CDI for carbonyldiimidazole; $CH_3CN$ for acetonitrile; CI or DCI for desorption chemical ionization; DMF for dimethyl formamide; ESI for electrospray ionization; EtOAc for ethyl acetate; FAB for fast atom bombardment; FRIR for Fourier transform infrared spectroscopy; HPLC for high performance liquid chromatography; IR for infrared spectroscopy; MeOH for methanol; MHz for megahertz; MIC for microscope; MS for mass spectra; NaHMDS for sodium hexamethyldisilazide; NMR for nuclear magnetic resonance; $R_f$ for retention factor; $R_t$ for retention time; TBAF for tetrabutylammonium fluoride; THF for tetrahydrofuran; TLC for thin layer chromatography; TMS for trimethylsilyl; and TMSCl for trimethylsilyl chloride.

The starting material 6-O-methyl erythromycin A 1 (clarithromycin, commercially available as BLAXIN® from Abbott Laboratories) is protected at the 2' and 4" positions by reaction with a suitable hydroxy protecting reagent, such as described by T. W. Greene and P. G. M. Wuts in *Protective Groups in Organic Synthesis*, 2nd. ed., John Wiley & Son, Inc. 1991. Hydroxy protecting groups include, for example, acetic anhydride, benzoic anhydride, benzylchloroformate, hexamethyldisilazane, or trialkylsilyl chloride in an aprotic solvent.

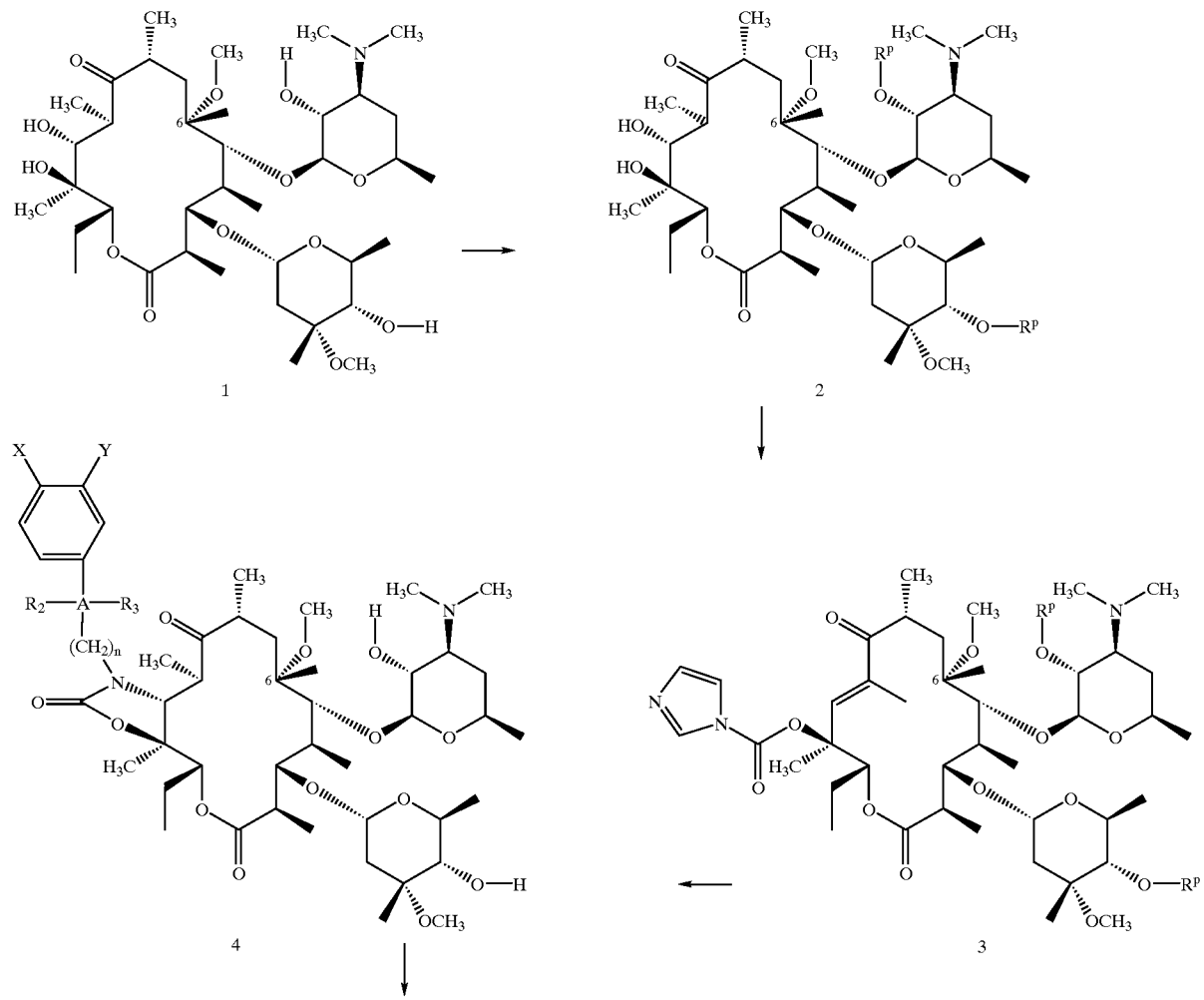

Scheme 1

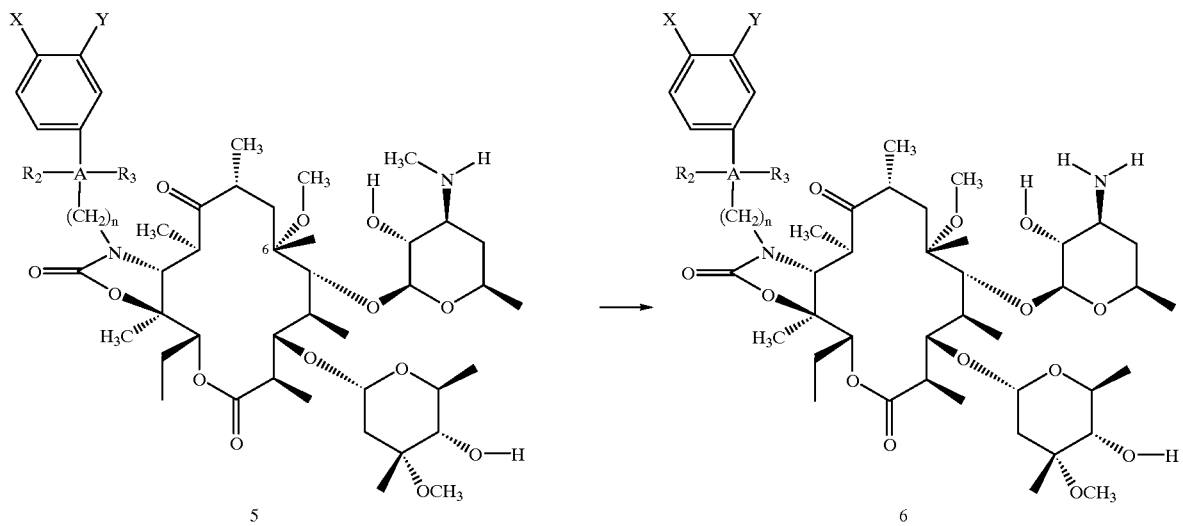

Protection of 2'- and 4"-hydroxy groups of 6-O-methyl-erythromycin A 1 as shown in Scheme 1 may be accomplished sequentially or simultaneously to provide compound 2 where $R^P$ is a hydroxy protecting group. A preferred protecting group $R^P$ is trimethylsilyl or acetyl.

Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof.

The protected compound 2 is treated with sodium hexamethyldisilazide or sodium hydride in an aprotic solvent at 0–25° C. and carbonyldiimidazole to yield compound 3. Treatment of compound 3 with an amino compound of the formula

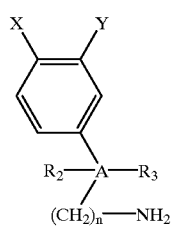

either without solvent or in acetonitrile at 25–80° C., followed by deprotection results in formation of N-substituted cyclic carbamate represented by compound 4.

Deprotection of the 2'- and 4"-hydroxy protecting groups to obtain compound 4 is carried out by the methods described by T. W. Greene and P. G. M. Wuts in *Protective Groups in Organic Synthesis*, 2nd. ed., John Wiley & Son, Inc. 1991. The desmethylation of the 3'-N-dimethyl group is accomplished by treating compound 4 with iodine in the presence of a suitable base, such as sodium acetate and a light or a heat source, followed by quench with sodium thiosulfate and work up to afford compound 5. The second methyl group is removed by treatment with iodine, a moderate base such as tribasic potassium phosphate and a light source to form the bisdesmethyl amine 6. N-Desmethylation can also be accomplished utilizing chloroformate reagents such as benzyl chloroformate, allyl chloroformate, vinyl chloroformate and the like.

Alkylation of 3',3'-N-bisdesmethyl compound 6 is achieved by reaction with an appropriate dialdehyde, ketonealdehyde or diketone in the presence of a hydride metal such as sodium cyanoborohydride or sodium triacetoxyborohydride or in the presence of Pd/C catalyst in a protic or non-protic solvent under hydrogen atmosphere. The dialdehydes, ketonealdehydes or diketones that may be used in preparing compound 7 include, for example, succinic dialdehyde, glutaraldehyde, acetonylacetone, 2,6-heptanedione, 3,6-octanedione, deca-1,9-dien-4,7-dione, 1,5-biscyclopropyl-1,5-dione. Alkylation of 3',3'-N-bisdesmethyl compound 6 can also be achieved by the reaction with an appropriate alkylating agent in the presence of a base by the methods known in the art to afford compound 7.

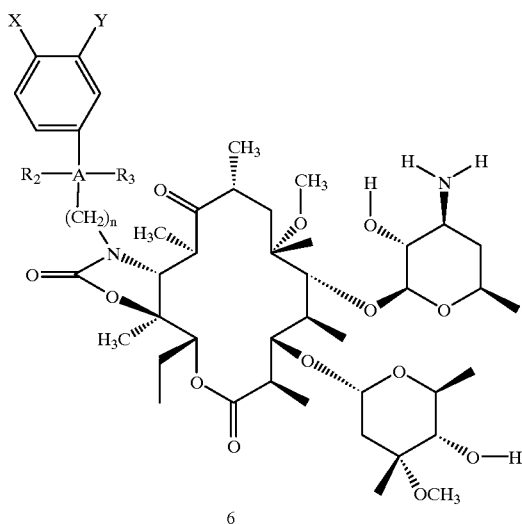

6

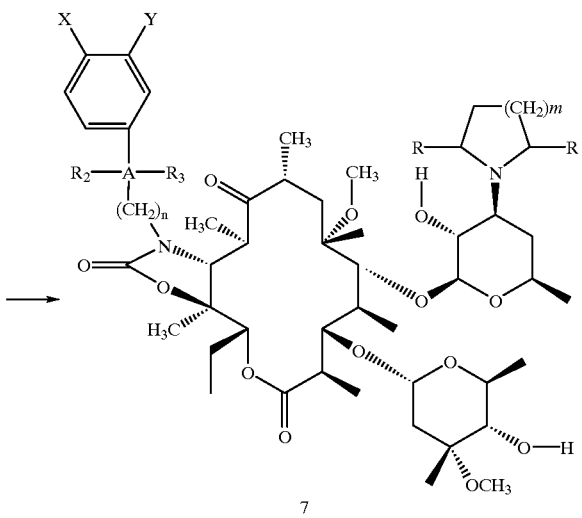

7

Scheme 2 illustrates a specific embodiment of Example 1 which involves treatment of 2'-acetyl-6-O-methyl erythromycin A 8 with trimethylsilyl chloride to afford compound 9. Compound 9 is treated with sodium hexamethyldisilazide and carbonyldiimidazole to yield the 12-O-acylimidazole derivative 10, which is subsequently reacted with 3,4-dichlorophenethyl amine to form the 11,12-cyclic carbamate derivative. The 11,12 cyclic carbamate so obtained is treated with methanol to give compound 11. Deprotection of the 4"-protected hydroxy group is achieved by methods known in the art to yield compound 12. Treatment of compound 12 with iodine in the presence of sodium acetate followed by quenching the reaction mixture with sodium bisulfite affords compound 13. The second desmethylation is achieved by treating 13 with iodine, tribasic potassium phosphate and a light source to form the bisdesmethyl amine 14. The alkylation of the 3'-nitrogen is achieved by reaction with succinic dialdehyde in the presence of sodium cyanoborohydride in methanol and a few drops of acetic acid to afford the final product, compound 15.

Scheme 2

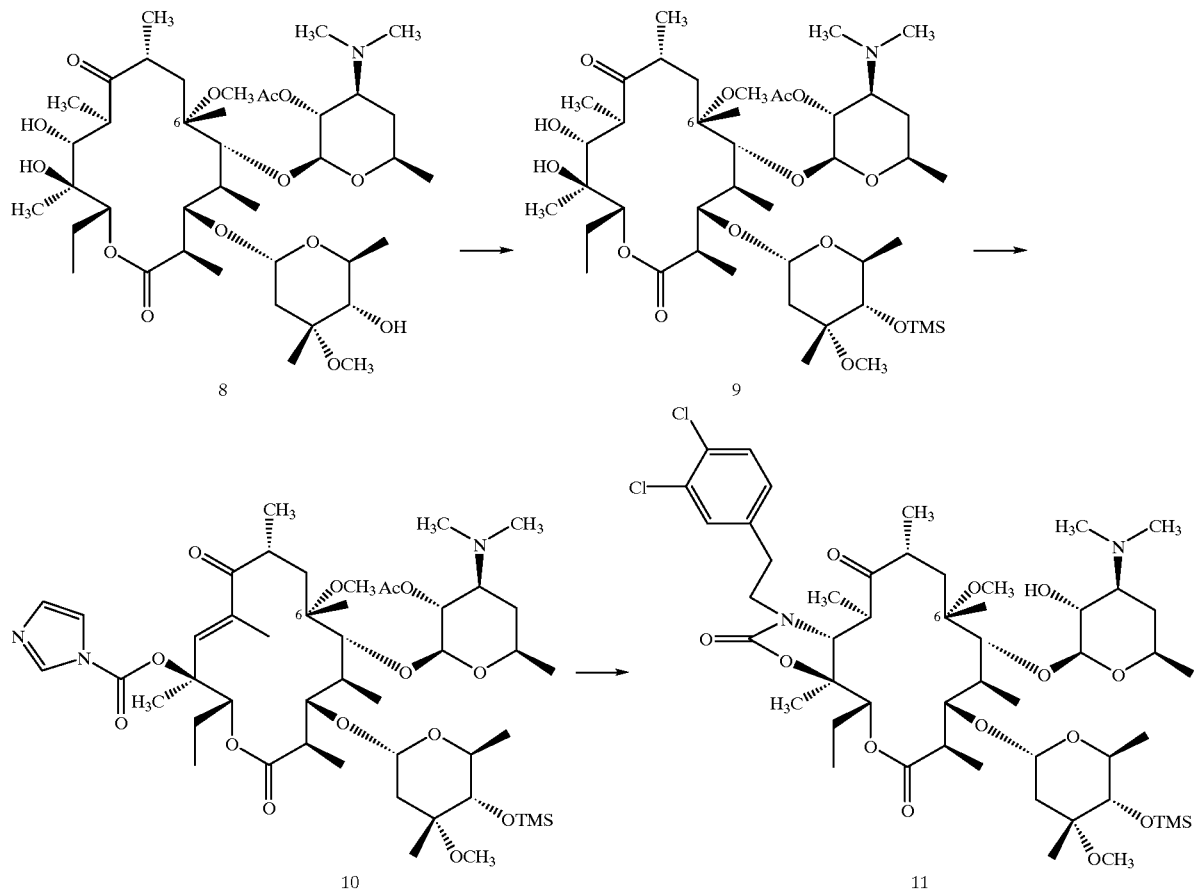

-continued
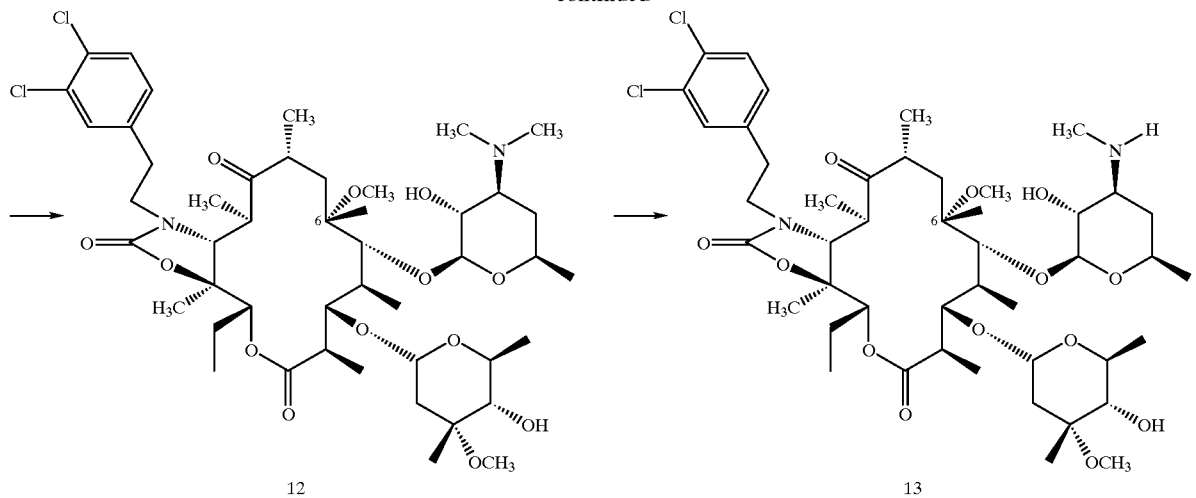
12 → 13
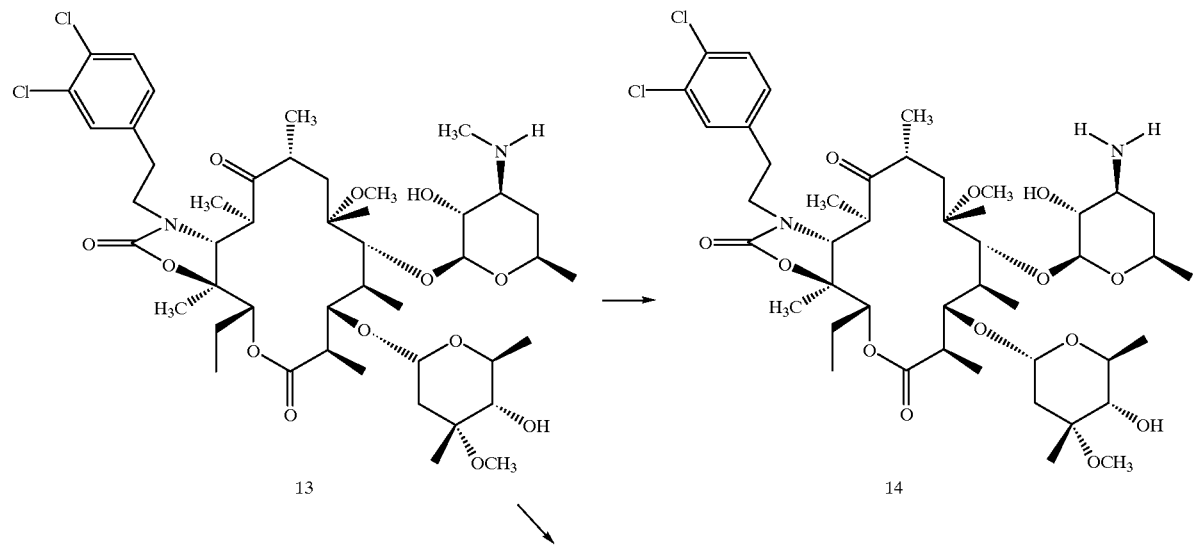
13 → 14
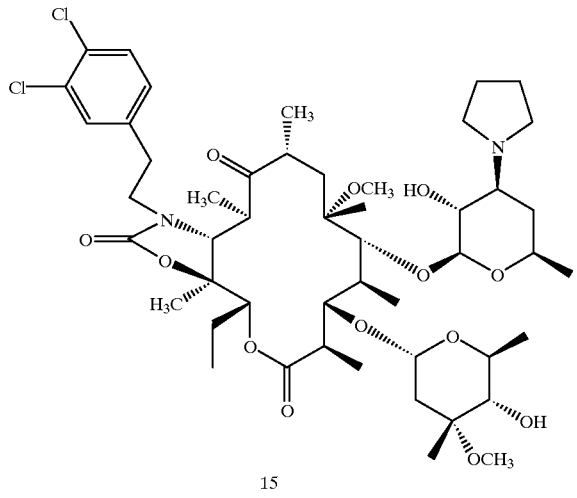
15

The foregoing may be better understood by reference to the following examples which are presented for illustration and not to limit the scope of the inventive concept.

EXAMPLE 1

3'-Desamino-(3'S)-N-pyrrolidinyl-11-deoxy-11-[carboxy-(3,4-dichlorophenethylamino)]-6-O-methyl-erythromycin A 11,12-(cyclic carbamate) (Compound 15, Scheme 2)

6-O-methyl erythromycin (commercially available from Abbott Laboratories as BIAXIN® was protected at the 2'- with the hydroxy protecting group by the methods described in the literature.

Step 1: 2'-O-Acetyl-4"-O-trimethylsilyl-6-O-methyl-erythromycin A (Compound 9, Scheme 2)

2'-O-Acetyl-6-O-methyl-erythromycin A (Compound 8, Scheme 2) (45 g, 57 mmol) was dissolved in 450 mL of $CH_2Cl_2$ and cooled to 0–5° C. in an ice/water bath. Pyridine (13.8 mL, 171 mmol) was added in one portion followed by the dropwise addition of TMSCl (14.5 mL, 114 mmol) over a 15 min period. The reaction was stirred for 1 h under the protection of a drying tube, after which TLC ($CH_2Cl_2$:MeOH, 9:1) indicated complete conversion to a new, less polar material. The reaction was then quenched with 500 mL of 0.5 M $NaH_2PO_4$, the organic layer separated and washed with $H_2O$ (300 mL), $NaHCO_3$(sat.) (300 mL), $H_2O$ (300 mL), and brine (100 mL), prior to drying ($Na_2SO_4$), filtering and concentrating. The residue was crystallized from $CH_3CN$ to yield 48 g of 9 (98%); mp 235–237° C. ($CH_3CN$); $R_f$=0.5 ($CH_2Cl_2$:MeOH, 9:1); MS ESI $(M+H)^+$ at m/z 862; $^{13}C$ NMR (75 MHz, $CDCl_3$) δ 221.0, 175.6, 169.9, 100.0, 96.0, 80.5, 80.3, 78.3, 77.8, 76.4, 74.1, 73.2, 72.0, 69.0, 67.1, 65.2, 62.7, 50.3, 49.4, 45.1, 44.9, 40.5, 38.7, 38.6, 37.1, 35.6, 30.9, 22.1, 21.5, 21.4, 20.9, 19.7, 19.2, 17.8, 15.9, 15.8, 12.1, 10.4, 8.9, 0.8.

Step 2: 4"-O-Trimethylsilyl-11-deoxy-11-[carboxy-(3,4-dichlorophenethylamnino)]-6-O-methyl-erythromycin A 11,12-(cyclic carbamate) (Compound 11, Scheme 2)

Compound 9 from Step 1 (20.4 g, 24.2 mmol) was dissolved in 20 mL of anhydrous THF then diluted with 200 mL of DMF. The resulting solution was cooled in an ice/water bath and treated with 1,1'-carbonyldiimidazole (19.6 g, 120.9 mmol) in one portion followed by the portionwise addition of 1.45 g (36 mmol) NaH (60% oil suspension). The reaction was allowed to warm to ambient temperature and was stirred under $N_2$ for 1 h after which TLC [EtOAc:MeOH, 95:5, Ce (IV) visualization] indicated complete conversion to a more polar material. The reaction was carefully quenched with water and then partitioned between EtOAc (400 mL) and water (300 mL). The organic phase was collected and washed with 1N NaOH (300 mL), water (2×300 mL), and brine (200 mL) prior to drying ($Na_2SO_4$) and concentration. A sample of the resulting colorless foam was submitted for mass spec analysis which showed $(M+H)^+$ at m/z 938 for the desired compound 10. The material was dissolved in $CH_3CN$ (25 mL), treated with 7.0 g (36 mmol) of 3,4-dichlorophenethylamine and stirred under $N_2$ at 55° C. After 48 h TLC [EtOAc:MeOH, 95:5, Ce (IV) visualization] indicated complete conversion of the starting compound to a less polar material which precipitated upon cooling to ambient temperature.

The resulting precipitate was recrystallized from $CH_3CN$ to yield 16.1 g of 2',4"-protected cyclic carbamate as colorless needles. This protected cyclic carbamate (16.1 g, 15.2 mmol) was suspended in 250 mL of methanol and the suspension heated to 55° C. under the protection of a drying tube. After 24 h TLC [$CH_2Cl_2$:MeOH, 9:1, Ce (IV) visualization] indicated complete conversion of the starting compound to a new more polar material which precipitated upon cooling to ambient temperature. The resulting solid was crystallized from MeOH/water to yield 13 g of compound 11: mp 112–114° C.; $R_f$=0.65 ($CH_2Cl_2$:MeOH, 9:1); MS (ESI) $(M+H)^+$ at m/z 1017; HRMS at m/z $(M+H)^+$ calcd 999.5116, obsd 999.5110; $^1H$ NMR (300 MHz, $CDCl_3$) δ 7.46 (d J=2 Hz, Ar H), 7.35 (d, J=8 Hz, Ar H), 7.19 (dd, J=8, 2 Hz, Ar H), 4.91 (d, J=4.4 Hz, 1H), 4.56 (d, J=7 Hz, 1H, C-1' CH), 3.75 (d, J=10 Hz, 1H, C-3 CH), 3.70 (s, 1H, C-11 CH), 3.67 (d, J=8 Hz, 1H, C-5 CH), 3.31 (s, 3H, C-6 $OCH_3$), 3.07 (s, 3H, C-6 $OCH_3$), 2.38 (d, J=15 Hz, 1H, C-2" CH), 2.28 (s, 6H, C-2' $N(CH_3)_2$), 1.43 (s, 3H, C-6 $CH_3$), 1.40 (s, 3H, C-12 $CH_3$), 1.07 (d, J=2.3 Hz, 3H, C-10 $CH_3$), 0.82 (t, J=7 Hz, 3H, C-15 $CH_3$), 0.16 (s, 9H, C-4" $OSi(CH_3)_3$); $^{13}C$ NMR (75 MHz, $CDCl_3$) δ 216.1, 176.5, 157.2, 139.3, 132.1, 131.0, 130.2, 130.0, 128.4, 102.4, 96.6, 82.8, 80.6, 79.9, 79.0, 78.0, 76.1, 73.1, 71.1, 68.0, 65.2, 64.7, 60.3, 50.6, 49.6, 45.5, 45.3, 44.8, 40.0 (2C), 39.1, 38.9, 35.6, 32.6, 28.6, 22.1, 21.8, 21.7, 20.1, 19.2, 18.8, 16.0, 14.1, 14.0, 10.2, 9.0, 0.8.

Step 3: 11-deoxy-11-[carboxy-(3,4-dichlorophenethylamino)]-6-O-methyl-erythromycin A 11,12-(cyclic carbamate) (Compound 12, Scheme 2)

The compound 11 from the above step (2.51 g, 2.46 mmol) was dissolved in 20 mL of THF, treated with 2.6 mL of TBAF (1 M/THF, 2.6 mmol), and stirred at ambient temperature. After 2 h TLC [$CHCl_3$:MeOH:$NH_4OH$, 90:8:1, Ce (IV) visualization] indicated complete conversion of the starting material to a new more polar material. The reaction mixture was partitioned between EtOAc (300 mL) and water (300 mL). The organic phase was washed with $NaHCO_3$ (sat., 200 mL), water (200 mL), and brine (200 mL) prior to drying ($Na_2SO_4$) and concentrating. The resulting residue crystallized from $CH_3CN$ to yield 1.5 g of product 12 (64%): mp 240–243° C.; $R_f$=0.45 ($CHCl_3$:MeOH:$NH_4OH$, 90:8:1); MS (FAB) $(M+H)^+$ at m/z 945; $^1H$ NMR (300 MHz, $CDCl_3$) δ 7.45 (d, J=2 Hz, 1H, Ar H), 7.35 (d, J=8 Hz, 1H. Ar H), 7.19 (dd, J=8, 2 Hz, 1H. Ar H), 4.44 (d, J=7 Hz, 1H, C-1' CH), 3.75 (d, J=10 Hz, 1H, C-3 CH), 3.69 (s, 1H, C-11 CH), 3.33 (s, 3H, C-3" $OCH_3$), 3.07 (s, 3H, C-6 $OCH_3$), 2.29 (s, 6H, C-3' $N(CH_3)_2$), 2.19 (d, J=10 Hz, 1H, C-4" OH), 1.44 (s, 3H, C-6 $CH_3$), 1.40 (s, 3H, C-12 $CH_3$), 1.31 (d, J=6 Hz, 3H, C-6" $CH_3$), 1.26 (s, 3H, C-3" $CH_3$), 1.15 (d, J=7 Hz, 3H, C-8 $CH_3$), 1.12 (d, J=8 Hz, 3H, C-4 $CH_3$), 1.02 (d, J=7 Hz, 3H, C-10 $CH_3$), 0.83 (t, J=8 Hz, 3H, C-15 $CH_3$); $^{13}C$ NMR (75 MHz, $CDCl_3$) δ 216.2, 176.4, 157.2, 139.3, 132.1, 131.0, 130.2, 130.1, 128.4, 102.9, 96.2, 82.8, 80.1, 78.9, 77.9, 77.8, 76.2, 72.6, 70.9, 68.9, 65.8, 65.6, 60.3, 50.6, 49.5, 45.5, 45.3, 44.8, 40.2 (2C), 39.0, 38.9, 34.8, 32.6, 28.5, 21.9, 21.5 (2C), 20.2, 18.9, 18.7, 16.0, 14.2, 14.1, 10.2, 9.0; IR (KBr) υ 3430, 2970, 2940, 1760, 1735, 1710, 1460, 1420, 1380, 1235, 1170, 1070, 1055, 1010, 1000 $cm^{-1}$; Anal. Calcd for $C_{47}H_{74}Cl_2N_2O_{13}$. 0.5 $H_2O$: C, 59.11; H, 7.91; N, 2.93. Found: C, 59.13; H, 8.12; N, 2.89.

Step 4: 3'-N-desmethyl-11-deoxy-11-[carboxy-(3,4-dichlorophenethylamino)]-6-O-methyl-erythromycin A 11.12-(cyclic carbamate) (Compound 13, Scheme 2)

2.5 g of the compound 12 from Step 3 (2.65 mmol) was dissolved in 50 mL of methanol and treated with 1.80 g of $NaOAc.3H_2O$ (13.25 mmol) and 0.71 g of $I_2$ (2.78 mmol). The solution was irradiated with a 500W halogen work lamp which maintaned the reaction at reflux temperature. After 2 h TLC indicated complete conversion of the starting compound to a new, more polar material. The excess $I_2$ was quenched by the dropwise addition of 1M $Na_2S_2O_3$. The reaction mixture was concentrated and the resulting residue partitioned between EtOAc (200 mL) and NaHCO$_3$ (sat) (200 mL). The organic phase was washed with brine (100 mL), dried (MgSO$_4$), filtered and concentrated. The resulting residue was purified on a silica gel column (elution with CHCl$_3$:MeOH:NH$_4$OH, 90:8:1) to yield 1.75 g of compound 13 (71%) as an amorphous solid: mp 136–142° C. (acetonitrile/water); R$_f$=0.33 (CHCl$_3$:MeOH:NH$_4$OH, 90:8:1); MS (FAB) (M+H)$^+$ at m/z 931; $^1$H NMR (300 MHz, CDCl$_3$) δ 7.45 (d, J=2 Hz, 1H, Ar H), 7.35 (d, J=8 Hz, 1H, Ar H), 7.19 (dd, J=8, 2 Hz, 1H, Ar H), 4.42 (d, J=7 Hz, 1H, C-1' CH), 3.74 (d, J=9 Hz, 1H, C-3 CH), 3.69 (s, 1H, C-11 CH), 3.32 (s, 3H, C-3" OCH$_3$), 3.07 (s, 3H, C-6 OCH$_3$), 2.42 (s, 3H, C-3' NCH$_3$), 1.44 (s, 3H, C-6 CH$_3$), 1.41 (s, 3H, C-12 CH$_3$), 1.31 (d, J=6 Hz, 3H, C-6" CH$_3$), 1.26 (s, 3H, C-3" CH$_3$), 1.16 (d, J=7 Hz, 3H, C-8 CH$_3$), 1.07 (d, J=8 Hz, 3H, C-4 CH$_3$), 1.03 (d, J=7 Hz, 3H, C-10 CH$_3$), 0.82 (t, J=7 Hz, 3H, C-15 CH$_3$); $^{13}$C NMR (75 MHz, CDCl$_3$) δ 216.2, 176.2, 157.1, 139.2, 132.2, 131.0, 130.3, 130.2, 128.4, 102.4, 96.2, 82.7, 80.5, 78.8, 77.8, 77.7, 76.3, 75.0, 72.7, 68.6, 65.7, 60.3, 50.7, 50.6, 49.5, 45.4, 45.3, 44.8, 39.0, 38.9, 38.8, 37.3, 34.8, 33.3, 32.6, 21.9, 21.5, 21.3, 20.1, 18.9, 18.7, 16.0, 14.2, 14.1, 10.2, 9.6; IR (KBr) υ 3420, 2970, 2940, 1760, 1735, 1710, 1460, 1420, 1380, 1235, 1170, 1065, 1050, 1010, 1000 cm$^{-1}$; Anal. Calcd for C$_{46}$H$_{72}$Cl$_2$N$_2$O$_{13}$. 0.75 H$_2$O: C, 56.39; H, 7.44; N, 2.81. Found: C, 56.63; H, 7.36; N, 2.78.

Step 5: 3',3'-N-Bisdesmethyl-11-deoxy-11-[carboxy-(3,4-dichlorophenethylamino)]-6-O-methyl-erythromycin A 11,12-(cyclic carbamate) (Compound 14, Scheme 2)

A solution of 2.07 g (2.19 mmol) of 13 was dissolved in 50 mL of methanol and treated dropwise with a solution of 2.32 g of K$_3$PO$_4$ (11.0 mmol) in 5 mL H$_2$O and 1.11 g of I$_2$ (4.38 mmol). The solution was irradiated with a 500 W halogen work lamp which maintained the reaction at reflux temperature. After 0.75 h the iodine color had dissipated and reverse phase HPLC indicated partial conversion to a new, more polar material. The reaction mixture was concentrated to ⅓ volume and partitioned between ethyl acetate (400 mL) and saturated sodium bicarbonate solution (100 mL). The organic layer was washed with water (300 mL) and brine (300 mL) prior to drying (Na$_2$SO$_4$), filtering and concentrating. The resulting residue was resubjected to the reaction conditions described above. After 1 h the iodine color had dissipated and reverse phase HPLC indicated total conversion to a new, more polar material. The reaction mixture was concentrated to ⅓ volume and partitioned between ethyl acetate (400 mL) and saturated sodium bicarbonate solution (100 mL). The organic layer was washed with water (300 mL) and brine (300 mL) prior to drying (Na$_2$SO$_4$), filtering and concentrating. The resulting residue was crystallized from CH$_3$CN to yield 1.25 g 14 (62%): MS (FAB) (M+H)$^+$ at m/z 917; $^1$H NMR (300 MHz, CDCl$_3$) δ 7.46 (d, J=2 Hz, Ar H), 7.35 (d, J=8 Hz, Ar H), 7.19 (dd, J=8, 2 Hz, Ar H), 4.39 (d, J=7 Hz, C-1' CH), 4.04–3.98 (m, 1H, C-5" CH), 3.32 (s, 3H, C-3" OCH$_3$), 2.68–2.61 (m, 1H, C-8 CH), 1.44 (s, 3H, C-6 CH$_3$), 1.41 (s, 3H, C-12 CH$_3$), 1.06 (d, J=8 Hz, 3H, C-4 CH$_3$), 1.03 (d, J=7 Hz, 3H, C-10 CH$_3$), 0.83 (t, J=7 Hz, 3H, C-15 CH$_3$); $^{13}$C NMR (75 MHz, CDCl$_3$) δ 216.0, 176.1, 157.1, 139.1, 132.1, 130.9, 130.2, 130.1, 128.3, 102.3, 96.1, 82.7, 80.5, 78.8, 77.8, 77.7, 77.3, 76.3, 72.6, 68.5, 65.7, 60.3, 52.4, 50.6, 49.3, 45.3, 45.2, 44.7, 41.3, 38.9, 38.7, 34.7, 32.5, 21.8, 21.4, 21.0, 20.0, 18.8, 18.6, 15.9, 14.2, 14.1, 10.1, 9.6; IR (Kbr) υ 3440, 2970, 2930, 1760, 1735, 1165, 1065, 1010 cm$^{-1}$; Anal. Calcd for C$_{45}$H$_{70}$Cl$_2$N$_2$O$_{13}$ (0.25 CHCl$_3$): C, 57.34; H, 7.47; N, 2.95. Found: C, 57.27; H, 7.26; N, 2.82.

Step 6: 3'-Desamino-3'-N-pyrrolidinyl-11-deoxy-11-[carboxy-(3,4-dichlorophenethylamino)]-6-O-methyl-erythromycin A 11,12-(cyclic carbamate) (Compound 15, Scheme 2)

150 mg (0.16 mmol) of 14 was dissolved in 10 mL of methanol and treated with succinic dialdehyde (0.2 mL, 40% solution in water), sodium cyanoborohydride (60 mg, 1.0 mmol) and acetic acid (2 drops to pH 5–6) and the mixture stirred at ambient temperature. After 24 h TLC [CHCl$_3$:MeOH, 98:2, Ce (IV) visualization] indicated complete conversion to a new, less polar material. The reaction was concentrated and the resulting residue partitioned between ethyl acetate (150 mL) and sodium bicarbonate (150 mL) (sat). The organic layer was washed with water (150 mL), and brine (150 mL) prior to drying (Na$_2$SO$_4$), filtering and concentrating. Minor impurities from the foamy residue were removed by conversion of product to the HCl salt and precipitation from EtOAc and diethylether: R$_f$=0.59 (CHCl$_3$:MeOH:NH$_4$OH, 84:15: 1); $^1$H NMR (CDCl$_3$) δ 7.46 (d, J=2 Hz, 1H), 7.35 (d, J=8 Hz, 1H), 7.19 (dd, J=8, 2 Hz, 1H), 4.92–4.88 (series of m, 2H), 4.45 (d, J=7 Hz, 1H), 4.03–4.00 (m, 1H), 3.89–3.76 (m, 2H), 3.74 (d, J=9 Hz, 1H), 3.71–3.63 (series of m, 4H), 3.54–3.49 (m, 1H), 3.33 (s, 3H), 3.32–3.28 (m, 1H), 3.12 (q, J=7 Hz, 1H), 3.07–2.97 (series of m, 5H), 2.93–2.62 (series of m, 6H), 2.38–2.24 (series of m, 3H), 1.94–1.50 (series of m, 11H), 1.43 (s, 3H), 1.40 (s, 3H), 1.30 (d, J=6 Hz, 3H), 1.26 (s, 3H), 1.24–1.21 (series of m, 7H), 1.16 (d, J=7 Hz, 3H), 1.11 (d, J=8 Hz, 3H), 1.03 (d, J=7 Hz, 3H), 0.82 (t, J=7 Hz, 3H); $^{13}$C NMR (CDCl$_3$) δ 216.3, 176.4, 157.2, 139.3, 132.2, 131.0, 130.3, 130.1, 128.4, 102.8, 96.2, 82.8, 80.2, 78.9, 78.0, 77.9, 76.3, 72.6, 72.3, 68.6, 65.8, 61.6, 60.4, 50.6, 49.5, 48.1, 45.5, 45.3, 44.8, 39.1, 39.0, 39.0, 34.9, 32.6, 30.1, 23.5, 21.9, 21.5, 21.4, 20.1, 18.8, 18.7, 16.0, 14.2, 14.1, 10.2, 9.3, 9.1; MS (ESI) (M+H)$^+$ at m/z 971.

EXAMPLE 2

3'-Desamino-3'-N-pyrrolidinyl-11-deoxy-11-[carboxy-(3-chloro-4-fluorophenethylamino)]-6-O-methyl-erythromycin A 11,12-(cyclic carbamate)

The title compound was prepared according to the process described in Example 1 but substituting 3-chloro-4-fluorophenethylamine for 3,4-dichlorophenethylamine. The product was purified by silica gel column chromatography (CHCl$_3$ to 3% MeOH/CHCl$_3$): $^{13}$C NMR (CDCl$_3$) δ 216.4, 176.4, 156.8 (J=246 Hz), 157.3, 136.1, 136.0, 131.0, 128.6 (J=17 Hz), 116.3 (J=21 Hz), 102.9, 96.2, 82.9, 80.2, 79.0, 78.0, 77.9, 76.3, 72.7, 72.4, 68.7, 65.8, 61.5, 60.4, 50.7, 49.5, 47.9, 45.5, 45.3, 45.0, 39.1, 39.1, 39.1, 39.0, 34.9, 32.5, 29.9, 23.6, 21.9, 21.5, 21.5, 21.0, 20.2, 18.9, 18.7, 16.0, 14.2, 14.1, 10.3, 9.1; MS (APCI) (M+H)$^+$ at m/z 956.

EXAMPLE 3

3'-Desamino-3'-N-piperidinyl-11-deoxy-11-[carboxy-(3,4-dichlorophenethylamino)]-6-O-methyl-erythromycin A 11,12-(cyclic carbamate)

The title compound was prepared according to the process described in Example 1 but substituting glutaraldehyde for succinic dialdehyde. The product was purified by a silica gel column chromatography (CHCl$_3$ to 3% MeOH/CHCl$_3$): MS (APCI) (M+H)$^+$ at m/z 985.

EXAMPLE 4

3'-Desamino-3'-N-piperidinyl-11-deoxy-11-[carboxy-(3-chloro-4-fluorophenethylamino)]-6-O-methyl-erythromycin A 11,12-(cyclic carbamate)

The title compound was prepared according to the process described in Example 2 but substituting glutaraldehyde for succinic dialdehyde. The product was purified by a silica gel column chromatography (CHCl$_3$ to 3% MeOH/CHCl$_3$): IR (KBr) υ 3454, 2937, 1761, 1736, 1711, 1502, 1457, 1380, 1168, 1105, 1062, 1012 cm$^{-1}$; $^{13}$C NMR (100 MHz, CDCl$_3$) δ 216.2, 176.3, 157.0, 156.6 (d, J=246 Hz), 135.9 (d, J=3 Hz), 130.9, 128.4 (d, J=7 Hz), 120.3 (d, J=18 Hz), 116.2 (d, J=21 Hz), 102.7, 96.1, 82.7, 79.8, 78.8, 77.8, 77.7, 76.0, 72.5, 69.9, 68.9, 66.8, 65.7, 65.6, 60.2 (2C), 50.5, 49.7, 49.6, 49.3, 45.4, 45.1, 44.8, 38.9, 38.8, 34.7, 32.3, 29.9, 26.4, 24.5, 21.7, 21.3 (2C), 20.0, 18.7, 18.5, 15.8, 14.0, 13.9, 10.1, 8.7; MS (FAB) (M+H)$^+$ at m/z 969; Anal. Calcd for C$_{51}$H$_{78}$Cl$_2$N$_2$O$_{13}$. 0.1 CHCl$_3$: C, 61.18; H, 8.01; N, 2.85. Found: C, 61.05; H, 7.82; N, 2.97.

EXAMPLE 5

3'-Desamino-3'S-N-(2,5-dimethylpyrrolidinyl)-11-deoxy-11-[carboxy-(3,4-dichlorophenethylamino)]-6-O-methyl-erythromycin A 11,12-(cyclic carbamate)

This material was prepared similarly as described in Example 3 but substituting acetonylacetone for glutaraldehyde and increasing reaction time up to 3 days and raising temperature (to reflux point). The crude product was purified on a silica gel column (CHCl$_3$ to MeOH:CHCl$_3$, 2:98) providing the following two diastereomers:

3'-Desamino-3'-N-(cis-2,5-dimethylpyrrolidinyl)-11-deoxy-11-[carboxy-(3,4-dichlorophenethylamino)]-6-O-methyl-erythromycin A 11,12-(cyclic carbamate)

This diastereomer was isolated as the less polar fraction on silica gel column (CHCl$_3$ to MeOH:CHCl$_3$, 2:98): mp 258–260° C. (acetonitrile); IR (MIC) υ 3472, 2968, 1752, 1735, 1458, 1168, 1068, 1013 cm$^{-1}$; $^{13}$C NMR (CDCl$_3$) δ 216.36, 176.39, 157.19, 139.31, 132.17, 131.02, 130.25, 130.12, 128.38, 103.31, 96.04, 82.81, 80.24, 78.93, 77.97, 77.75, 76.22, 72.65, 72.18, 69.10, 65.75, 60.88, 60.36, 58.09, 52.38, 50.66, 49.48, 45.59, 45.27, 44.80, 39.13, 39.05, 38.97, 34.86, 32.84, 32.63, 32.17, 30.04, 24.39, 21.91, 21.62, 21.50, 21.47, 20.16, 18.88, 18.69, 15.99, 14.15, 14.12, 10.22, 8.96. MS (APCI) (M+H)$^+$ at m/z 999; Anal. Calcd. for C$_{51}$H$_{80}$Cl$_2$N$_2$O$_{13}$: C, 61.25; H, 8.06; N, 2.80. Found: C, 61.49; H, 8.01; N, 2.69.

3'-Desamino-3'-N-(trans-2,5-dimethylpyrrolidinyl-11-deoxy-11-[carboxy-(3,4-dichlorophenethylamino)]-6-O-methyl-erythromycin A 11,12-(cyclic carbamate)

This diastereomer was isolated as more polar fraction on silica gel column (CHCl$_3$ to MeOH:CHCl$_3$, 2:98): IR (MIC) υ 3451, 2969, 1761, 1736, 1459, 1168, 1067, 1013 cm$^{-1}$;. MS (APCI) at m/z 999 (M+H)$^+$.

EXAMPLE 6

3'-Desamino-3'-N-(2,5-dimethylpyrrolidinyl)-11-deoxy-11-[carboxy-(3-chloro-4-fluorophenethylamino)]-6-O-methyl-erythromycin A 11,12-(cyclic carbamate)

This material was prepared similarly as described in Example 4 but substituting acetonylacetone for glutaraldehyde and increasing reaction time up to 3 days and raising temperature (to reflux point). The crude product was purified on a silica gel column (CHCl$_3$ to MeOH:CHCl$_3$, 2:98) providing the following two diastereomers:

3'-Desamino-3'-N-(cis-2,5-dimethylpyrrolidinyl)-11-deoxy-11-[carboxy-(3-chloro-4-fluorophenethylamino)]-6-O-methyl-erythromycin A 11,12-(cyclic carbamate)

This diastereomer was isolated as less polar fraction on silica gel column (CHCl$_3$ to MeOH/CHCl$_3$, 2:98): mp 276–8° C. (acetonitrile); IR (MIC) υ 3456, 2970, 1758, 1459, 1168, 1067, 1013 cm$^{-1}$ $^{13}$C NMR (CDCl$_3$) δ 216.41, 176.40, 157.20, 156.75 (d, J=247 Hz), 136.01 (d, J=3.8 Hz), 131.02, 128.54 (d, J=7 Hz), 120.48 (d, J=17 Hz), 116.31 (d, J=21 Hz), 103.28, 96.00, 82.79, 80.22, 78.91, 77.95, 77.70, 76.21, 72.63, 72.15, 69.09, 65.71, 60.84, 60.29, 58.06, 52.34, 50.69, 49.49, 45.61, 45.25, 44.98, 39.11, 39.03, 38.96, 34.84, 32.82, 32.49, 32.17, 29.98, 24.39, 21.90, 21.61, 21.51, 21.46, 20.17, 18.89, 18.68, 16.01, 14.17, 14.14, 10.24, 8.96; MS (APCI) (M+H)$^+$ at m/z 983; Anal. Calcd. for C$_{51}$H$_{80}$ClFN$_2$O$_{13}$: C, 62.27; H, 8.20; N, 2.85. Found: C, 62.46; H, 8.06; N, 2.79.

3'-Desamino-3'-N-(trans-2,5-dimethylpyrrolidinyl)-11-deoxy-11-[carboxy-(3-chloro-4-fluorophenethylamino)]-6-O-methyl-erythromycin A 11,12-(cyclic carbamate)

This diastereomer was isolated as more polar fraction on silica gel column (CHCl$_3$ to MeOH:CHCl$_3$, 2:98): IR (MIC) υ 3451, 2970, 1761, 1736, 1458, 1168, 1065, 1012 cm$^{-1}$;. MS (APCI) at m/z 983 (M+H)$^+$.

EXAMPLE 7

3'-Desamino-3'-N-(2,6-dimethylpiperidinyl)-11-deoxy-11-[carboxy-(3,4-dichlorophenethylamino)]-6-O-methyl-erythromycin A 11,12-(cyclic carbamate)

This material was prepared similarly as described in Example 3 but substituting 2,6-heptadione for glutaraldehyde and increasing reaction time up to 3 days and raising temperature (to reflux point). The crude product was purified on a silica gel column (CHCl$_3$ to MeOH:CHCl$_3$, 2:98) providing the three diastereomers:

The least polar diastereomer: $^{13}$C NMR (CDCl$_3$) δ 216.06, 176.35, 157.20, 139.30, 132.17, 131.04, 130.26, 128.39, 103.31, 96.06, 82.83, 80.17, 78.88, 77.91, 77.79, 76.22, 72.65, 71.33, 69.15, 65.75, 60.10, 58.95, 50.68, 49.48, 45.88, 45.56, 45.25, 44.80, 39.12, 38.97, 38.91, 38.24, 34.84, 32.63, 21.91, 21.50, 20.16, 19.51, 18.88, 18.67, 16.03, 14.17, 14.14, 10.24, 9.01; MS (APCI) (M+H)$^+$ at m/z 1013.

The second least polar diastereomer: IR (MIC) υ 3307, 2969, 2934, 1760, 1735, 1654, 1456, 1415, 1167, 1053, 1014 cm$^{-1}$; $^{13}$C NMR (CDCl$_3$) δ 216.33, 176.31, 157.20, 139.30, 132.17, 131.04, 130.26, 128.39, 103.42, 95.99, 82.83, 80.17, 78.88, 77.83, 77.79, 76.22, 72.65, 69.81, 69.39, 65.75, 60.34, 58.95, 50.68, 49.48, 45.88, 45.56, 45.25, 44.80, 39.05, 38.97, 38.91, 35.70, 34.84, 32.63, 21.91, 21.50, 20.16, 19.07, 18.88, 18.67, 16.03, 14.17, 14.14, 10.24, 9.01; MS (APCI) (M+H)$^+$ at m/z 1013.

The most polar diastereomer: $^{13}$C NMR (CDCl$_3$) δ 216.40, 176.39, 157.21, 139.31, 132.18, 131.04, 130.26, 130.13, 128.40, .103.73, 96.08, 82.82, 80.25, 78.94, 77.92, 77.85, 76.24, 72.62, 71.80, 69.55, 65.79, 62.36, 60.34, 52.96, 51.56, 50.69, 49.53, 45.59, 45.28, 44.81, 39.14, 39.05, 38.98, 34.84, 33.77, 33.30, 32.63, 29.69, 23.99, 23.36, 21.91, 21.54, 21.48, 20.42, 20.19, 19.71, 18.89, 18.68, 16.01, 14.18, 14.13, 10.24, 8.99; MS (APCI) (M+H)$^+$ at m/z 1013.

EXAMPLE 8

3'-Desamino-3'-N-(2,6-dimethylpiperidinyl)-11-deoxy-11-[carboxy-(3-chloro-4-fluorophenethylamino)]-6-O-methyl-erythromycin A 11,12-(cyclic carbamate)

This material was prepared similarly as described in Example 4 but substituting 2,6-heptadione for glutaraldehyde and increasing reaction time up to 3 days and raising temperature (to reflux point). The crude product was purified on a silica gel column (CHCl$_3$ to MeOH:CHCl$_3$, 2:98) providing three diastereomers: the second least polar diastereomer: IR (MIC) υ 3441, 2971, 2935, 1761, 1736, 1502, 1458, 1380, 1168, 1054, 1013 cm$^{-1}$; MS (APCI) (M+H)$^+$ at m/z 997.

EXAMPLE 9

3'-Desamino-3'-N-(2,5-diethylpyrrolidinyl)-11-deoxy-11-[carboxy-(3,4-dichlorophenethylamino)]-6-O-methyl-erythromycin A 11,12-(cyclic carbamate)

The title compound was prepared in accordance with the method described in Example 3 but substituting 3,6-octadione for glutaraldehyde, and increasing reaction time up to 3 days and raising temperature (to reflux point). The crude product was purified on a silica gel column (CHCl$_3$:MeOH:NH$_4$OH, 90:8:1) to yield desired product as an amorphous solid: MS (APCI) (M+H)$^+$ at m/z 1027.

EXAMPLE 10

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate)

The title compound was prepared in accordance with the method described in Example 2 but substituting 3,6-octadione for succinic dialdehyde, and increasing reaction time up to 3 days and raising temperature (to reflux point). The crude product was purified on a silica gel column (CHCl$_3$:MeOH:NH$_4$OH, 90:8:1) to yield the desired product as an amorphous solid: IR (KBr) υ 2968, 2936, 1759, 1734, 1168, 1065, 1012 cm$^{-1}$; $^{13}$C NMR (CDCl$_3$) δ 214.59, 214.43, 174.43, 172.95, 155.21, 155.08, 154.74 (d, J=246 Hz), 153.54, 134.04 (d, J=3.7 Hz), 133.80, 133.76, 129.02, 128.99, 126.57 (d, J=6.8 Hz), 126.46, 114.35 (d, J=20.5 Hz), 114.30 (d, J=20.5 Hz), 102.48, 101.19, 96.00, 94.05, 80.81, 80.50, 80.20, 78.26, 78.08, 76.92, 74.56, 74.19, 70.64, 70.44, 63.73, 63.63, 58.56, 58.30, 48.68, 47.44, 47.30, 47.00, 44.68, 43.61, 43.24, 42.99, 42.74, 38.32, 37.13, 37.05, 36.95, 33.38, 32.84, 32.07, 30.60, 30.50, 27.66, 27.14, 19.89, 19.45, 19.20, 18.16, 17.12, 16.88, 16.69, 16.14, 14.45, 14.00, 12.84, 12.11, 10.87, 9.07, 8.61, 8.52, 8.23, 8.20, 6.98 (excess signals in NMR due to a mixture of diastereomers); MS (APCI) (M+H)$^+$ at m/z 1011; Anal. Calcd for C$_{53}$H$_{84}$ClFN$_2$O$_{13}$.0.5 CHCl$_3$: C, 59.97; H, 7.94; N, 2.61. Found: C, 60.45; H, 7.99; N, 2.89.

EXAMPLE 11

3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate)

Step 1: Glutaric bis(N,O-dimethylhydroxamide)

N,O-Dimethylhydroxylamine hydrochloride (29.265 g, 0.3 mol) was added to a solution of glutaryl dichloride (16.901 g, 0.1 mol) in dichloromethane (0.5 L) cooled to 0–5° C. followed by slow addition of triethylamine (80 mL). The reaction mixture was stirred for 1 hr and allowed slowly to warm up to room temperature. All volatiles were evaporated in vacuo and the residue partitioned between saturated NaHCO$_3$ solution (200 mL) and ethyl acetate (400 mL). The aqueous phase was extracted with ethyl acetate (3×200 mL) and the organic layer dried over anhydrous MgSO$_4$, filtered and concentrated in vacuo. The oily residue (65%) was used without further purification: $^1$H NMR (CDCl$_3$) δ 3.69 (s, 6H), 3.18 (s, 6H), 2.53 (t, J=7 Hz, 4H), 1.98 (quintet, J=7.2 Hz, 2H).

Step 2: 1,5-Biscyclopropyl-1,5-dione

Cyclopropyl bromide (1.21 g, 10 mmol) was added dropwise to a mixture of magnesium (0.268 g, 11 mmol) in dry tetrahydrofurane (with cat. I$_2$). After adding 10–20% of cyclopropylbromide, the reaction initiated and further addition of cyclopropylbromide maintained the reaction mixture at gentle reflux. The reaction mixture was heated at 40–50° C. for 2 hrs then cooled to 0–5° C. and glutaric bis-(N,O-dimethylhydroxamide) (0.655 g, 3 mmol) was added dropwise. The stirring was continued for 4 hr while the reaction mixture slowly warmed up to room temperature. The excess Grignard reagent was quenched with saturated NH$_4$Cl solution, the aqueous layer extracted with diethylether (2×), the combined organic layers dried over anhydrous MgSO$_4$, filtered and solvent evaporated in vacuo. The residue was purified by a silica gel column chromatography (dichloromethane) yielding a white solid product (0.76 g, 70%): $^1$H NMR (CDCl$_3$) δ 2.60 (t, J=7, Hz, 4H), 1.96–1.87 (m, 4H), 1.04–0.96 (m, 4H), 0.90–0.83 (m, 4H).

Step 3: 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate)

The compound was prepared in accordance with the method described in Example 4 but substituting 1,5-biscyclopropyl-1,5-dione for glutaraldehyde, and increasing reaction time up to 3 days and raising temperature (to reflux point). The crude product was purified by a silica gel column chromatography (CHCl$_3$ to 3% MeOH/CHCl$_3$): MS (APCI) (M+H)$^+$ at m/z 1049.

EXAMPLE 12

3'-Desamino-3'-N-(2,5-diallylpyrrolidinyl)-1-deoxy-11-[carboxy-(3,4-dichlorophenethylamino)]-6-O-methyl-erythromycin A 11,12-(cyclic carbamat Step 1: Succinic bis(N,O-dimethylhydroxamide):

N,O-Dimethylhydroxylamine hydrochloride (28.3 g, 0.29 mol) was added to a solution of succinyl dichloride (15.0 g, 0.097 mol) in dichloromethane (0.45 L) cooled to 0 to 5° C. followed by slow addition of triethylamine (81 mL). The reaction mixture was stirred for 1 hr and allowed to slowly warm up to room temperature. All volatiles were evaporated in vacuo and the residue partitioned between sat. NaHCO$_3$ solution (200 mL) and ethyl acetate (400 mL). The aqueous layer was extracted with ethyl acetate (3×200 mL) and the organic layer dried over anhydrous MgSO$_4$, filtered and concentrated in vacuo. The oily product (35%) solidified and was used in the next step without further purification: $^1$H NMR (CDCl$_3$) δ 3.74 (s, 6H), 3.20 (s, 6H), 2.78 (s, 4H); MS (DCI) (M+H)$^+$ at m/z 205.

Step 2: Deca-1,9-dien-4,7-dione:

To a stirred solution of succinic bis(N,O-dimethylhydroxamide) (1.5 g, 7.34 mmol) in dry tetrahydrofuran (30 mL) was cooled to −78° C. under nitrogen and allylmagnesium bromide (1 M solution in diethylether, 16.2 mmol) was added dropwise. The stirring continued for 1 hr at −78° C. and then for 1 hr at room temperature. The reaction mixture was quenched with saturated NH$_4$Cl solution, the water layer extracted with diethylether (2×), the combined organic extracts were dried over anhydrous MgSO$_4$, filtered and solvent evaporated in vacuo. The residue was purified by a silica gel column chromatography (chloroform) yielding a yellow oily material (0.48 g, 39%): $^1$H NMR (CDCl$_3$) δ 5.83–5.98 (m, 2 H), 5.12–5.21 (m, 4 H), 3.20–3.27 (m, 4H), 2.75 (s, 4H); MS (DCI) (M+NH$_4$)$^+$ at m/z 184.

Step 3: 3'-Desamino-3'-N-(2,5-diallylpyrrolidinyl)-11-deoxy-11-[carboxy-(3,4-dichlorophenethylamino)]-6-O-methyl-erythromycin A 11,12-(cyclic carbamate)

The title compound is prepared according to the method described in Example 3 but substituting deca-1,9-dien-4,7-dione for glutaraldehyde. After workup and purification 3'-desamino-3'-N-(2,5-diallylpyrrolidinyl)-11-deoxy-11-[carboxy-(3,4-dichlorophenethylamino)]-6-O-methyl-erythromycin A 11,12-(cyclic carbamate) is obtained.

EXAMPLE 13

3'-Desamino-3'-N-(2,5-diallylpyrrolidinyl)-11-deoxy-11-[carboxy-(3-chloro-4-fluorophenethylamino)]-6-O-methyl-erythromycin A 11,1 2-(cyclic carbamate)

The title compound is prepared in accordance with the method described in Example 2 but substituting deca-1,9-dien-4,7-dione for succinic dialdehyde. After workup and purification 3'-desamino-3'-N-(2,5-diallylpyrrolidinyl)-11-deoxy-11-[carboxy-(3-chloro-4-fluorophenethylamino)]-6-O-methyl-erythromycin A 11,12-(cyclic carbamate) is obtained.

EXAMPLE 14

3'-Desamino-3'-N-(2,5-dipropylpyrrolidinyl)-11-deoxy-11-[carboxy-(3-chloro-4-fluorophenethylamino)]-6-O-methyl-erythromycin A 11,12-(cyclic carbamate)

Step 1: 4,7-Decadione:

The title compound is prepared in accordance with the method described in Example 12, Step 2, but substituting propylmagnesium bromide for allylmagnesium bromide. After workup and purification 4,7-decadione is obtained.

Step 2: 3'-Desamino-3'-N-(2,5-dipropylpyrrolidinyl)-11-deoxy-[carboxy-(3-chloro-4-fluorophenethylamino)]-6-O-methyl-erythromycin A 11,12-(cyclic carbamate)

The compound is prepared in accordance with the method described in Example 13 but substituting 4,7-decadione for deca-1,9-dien-4,7-dione. After workup and purification 3'-desamino-3'-N-(2,5-dipropylpyrrolidinyl)-11-deoxy-11-[carboxy-(3-chloro-4-fluorophenethylamino)]-6-O-methyl-erythromycin A 11,12-(cyclic carbamate) is obtained.

EXAMPLE 15

3'-Desamino-3'-N-(2,5-dipropylpyrrolidinyl)-11-deoxy-11-[carboxy-(3,4-dichlorophenethylamino)]-6-O-methyl-erythromycin A 11,12-(cyclic carbamate)

The compound is prepared in accordance with the method described in Example 12 but substituting 4,7-decadione for deca-1,9-dien-4,7-dione. After workup and purification 3'-desamino-3'-N-(2,5-dipropylpyrrolidinyl)-11-deoxy-11-[carboxy-(3,4-dichlorophenethylamino)]-6-O-methyl-erythromycin A 11,12-(cyclic carbamate) is obtained.

EXAMPLE 16

3'-Desamino-3'-N-(2,5-diisopropylpyrrolidinyl)-11-deoxy-11-[carboxy-(3-chloro-4-fluorophenethylamino)]-6-O-methyl-erythromycin A 11,12-(cyclic carbamate)

Step 1: 2,7-Dimethyl-3,6-octadione:

The title compound is prepared in accordance with the method described in Example 12, Step 2, but substituting isopropylmagnesium bromide for allylmagnesium bromide. After workup and purification 2,7-dimethyl-3,6-octadione is obtained.

Step 2: 3'-Desamino-3'-N-(2,5-diisopropylpyrrolidinyl)-11-deoxy11-[carboxy-(3-chloro-4-fluorophenethylamino)]-6-O-methyl-erythromycin A 11,12-(cyclic carbamate)

The title compound is prepared in accordance with the method described in Example 13 but substituting 2,7-dimethyl-3,6-octadione for deca-1,9-dien-4,7-dione. After workup and purification 3'-desamino-3'-N-(2,5-diisopropylpyrrolidinyl)-11-deoxy-11-[carboxy-(3-chloro-4-fluorophenethylamino)]-6-O-methyl-erythromycin A 11,12-(cyclic carbamate) is obtained.

EXAMPLE 17

3'-Desamino-3'-N-(2,5-diisopropylpyrrolidinyl)-11-deoxy-11-[carboxy-(3,4-dichlorophenethylamino)]-6-O-methyl-erythromycin A 11,12-(cyclic carbamate)

The title compound is prepared in accordance with the method described in Example 12 but substituting 2,7-dimethyl-3,6-octadione for deca-1,9-dien-4,7-dione. After workup and purification 3'-desamino-3'-N-(2,5-diisopropylpyrrolidinyl)-11-deoxy-11-[carboxy-(3,4-dichlorophenethylamino)]-6-O-methyl-erythromycin A 11,12-(cyclic carbamate) is obtained.

EXAMPLE 18

3'-Desamino-3'-N-(2,5-biscyclopropylpyrrolidinyl)-11-deoxy-11-[carboxy-(3-chloro-4-fluorophenethylamino)]-6-O-methyl-erythromycin A 11,12-(cyclic carbamate)

Step 1: 1,4-Biscyclopropyl-1,4-butadione:

The title compound is prepared in accordance with the method described in Example 12, Step 2, but substituting cyclopropylmagnesium bromide (Example 11, Step 2) for allylmagnesium bromide. After workup and purification 1,4-biscyclopropyl-1,4-butadione is obtained.

Step 2: 3'-Desamino-3'-N-(2,5-biscyclopropylpyrrolidinyl)-11-deoxy-11-[carboxy-(3-chloro-4-fluorophenethylamino)]-6-O-methyl-erythromycin A 11,12-(cyclic carbamate)

The title compound is prepared in accordance with the method described in Example 13 but substituting 1,4-biscyclopropyl-1,4-butadione for deca-1,9-dien-4,7-dione. After workup and purification 3'-desamino-3'-N-(2,5-biscyclopropylpyrrolidinyl)-11-deoxy-11-[carboxy-(3-chloro-4-fluorophenethylamino)]-6-O-methyl-erythromycin A 11,12-(cyclic carbamate) is obtained.

EXAMPLE 19

3'-Desamino-3'-N-(2,5-biscyclopropylpyrrolidinyl)-11-deoxy-11-[carboxy-(3,4-dichlorophenethylamino)]-6-O-methyl-erythromycin A 11,12-(cyclic carbamate)

The title compound is prepared in accordance with the method described in Example 12 but substituting 1,4- biscyclopropyl-1,4-butadione for deca-1,9-dien-4,7-dione. After workup and purification 3'-desamino-3'-N-(2,5-biscyclopropylpyrrolidinyl)-11-deoxy-11-[carboxy-(3,4-dichlorophenethylamino)]-6-O-methyl-erythromycin A 11,12-(cyclic carbamate) is obtained.

EXAMPLE 20

3'-Desamino-3'-N-(2,5-biscyclobutylpyrrolidinyl)-11-deoxy-11-[carboxy-(3-chloro-4-fluorophenethylamino)]-6-O-methyl-erythromycin A 11,12-(cyclic carbamate)

Step 1: 1,4-Biscyclobutyl-1,4-butadione:

The title compound is prepared in accordance with the method described in Example 12, Step 2, but substituting cyclobutylmagnesium bromide for allylmagnesium bromide. After workup and purification 1,4-biscyclobutyl-1,4-butadione is obtained.

Step 2: 3'-Desamino-3'-N-(2,5-biscyclobutylpyrrolidinyl)-11-deoxy-11-[carboxy-(3-chloro-4-fluorophenethylamino)]-6-O-methyl-erythromycin A 11,12-(cyclic carbamate)

The title compound is prepared in accordance with the method described in Example 13 but substituting 1,4-biscyclobutyl-1,4-butadione for deca-1,9-dien-4,7-dione. After workup and purification 3'-desamino-3'-N-(2,5-biscyclobutylpyrrolidinyl)-11-deoxy- 11-[carboxy-(3-chloro-4-fluorophenethylamino)]-6-O-methyl-erythromycin A 11,12-(cyclic carbamate) is obtained.

EXAMPLE 21

3'-Desamino-3'-N-(2,5-biscyclobutylpyrrolidinyl)-11-deoxy-11-[carboxy-(3,4-dichlorophenethylamino)]-6-O-methyl-erythromycin A 11,12-(cyclic carbamate)

The title compound is prepared in accordance with the method described in Example 12 but substituting 1,4-biscyclobutyl-1,4-butadione for deca-1,9-dien-4,7-dione. After workup and purification 3'-desamino-3'-N-(2,5-biscyclobutylpyrrolidinyl)-11-deoxy-11-[carboxy-(3,4-dichlorophenethylamino)]-6-O-methyl-erythromycin A 11,12-(cyclic carbamate) is obtained.

EXAMPLE 22

3'-Desamino-3'-N-[2,5-bis(cyclopropylmethyl)pyrrolidinyl]-11-deoxy-11-[carboxy-(3-chloro-4-fluorophenethylamino)]-6-O-methyl-erythromycin A 11,12-(cyclic carbamate)

Step 1: 1,6-Biscyclopropyl-2,5-hexadione:

The title compound is prepared in accordance with the method described in Example 12, Step 2, but substituting cyclopropylmethylmagnesium bromide for allylmagnesium bromide. After workup and purification 1,6-biscyclopropyl-2,5-hexadione is obtained.

Step 2: 3'-Desamino-3'-N-[2,5-bis(cyclopropylmethyl)pyrrolidinyl]-11-deoxy-11-[carboxy-(3-chloro-4-fluorophenethylamino)]-6-O-methyl-erythromycin A 11,12-(cyclic carbamate)

The title compound is prepared in accordance with the method described in Example 13 but substituting 1,6-biscyclopropyl-2,5-hexadione for deca-1,9-dien-4,7-dione. After workup and purification 3'-desamino-3'-N-[2,5-bis(cyclopropylmethyl)pyrrolidinyl]-11-deoxy-11-[carboxy-(3-chloro-4-fluorophenethylamino)]-6-O-methyl-erythromycin A 11,12-(cyclic carbamate) is obtained.

EXAMPLE 23

3'-Desamino-3'-N-[25-bis(cyclopropylmethyl)pyrrolidinyl]-11-deoxy-11-[carboxy-(3,4-dichlorophenethylamino)]-6-O-methyl-erythromycin A 11,12-(cyclic carbamate)

The title compound is prepared in accordance with the method described in Example 12 but substituting 1,6-biscyclopropyl-2,5-hexadione for deca-1,9-dien-4,7-dione. After workup and purification 3'-desamino-3'-N-[2,5-bis(cyclopropylmethyl)pyrrolidinyl]-11-deoxy-11-[carboxy-(3,4-dichlorophenethylamino)]-6-O-methyl-erythromycin A 11,12-(cyclic carbamate) is obtained.

We claim:

1. A compound having the formula:

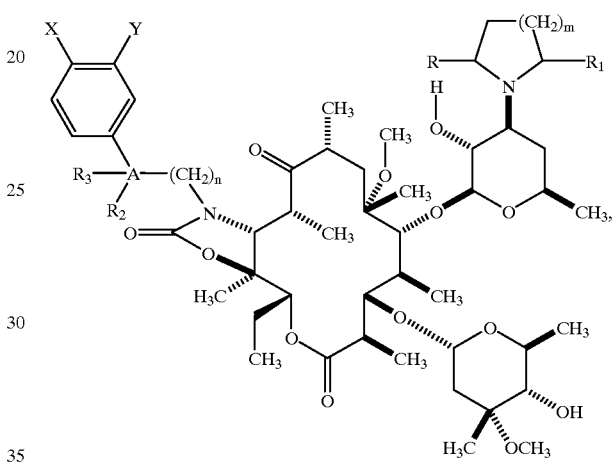

or a pharmaceutically acceptable salt or ester thereof, wherein

A is selected from the group consisting of:
(a) —C,
(b) —N, and
(c) —O;

X and Y are independently at each occurrence selected from the group consisting of:
(a) hydrogen,
(b) halide,
(c) alkoxy,
(d) alkyl,
(e) aryl, and
(f) substituted aryl;

R and $R_1$ are independently at each occurrence selected from the group consisting of:
(a) alkyl,
(b) cycloalkyl,
(c) heterocylic,
(d) substituted heterocyclic,
(e) alkylcycloalkyl,
(f) substituted alkylcycloalkyl,
(g) alkylaryl,
(f) alkylheterocyclic,
(g) alkenyl, and
(h) alkynyl, m is 1, 2 or 3

$R_2$ and $R_3$ are independently at each occurrence
(a) hydrogen,
(b) methyl, or R₂ and R₃ together form a cycloalkyl moiety, when A is C; and n=1, 2 or 3.

2. The compound according to claim 1, wherein R, and R₁ are independently an alkyl, cycloalkyl, or heterocyclic at each occurrence; X and Y are independently chloro, fluoro, dioxalano, hydrogen, or alkoxy; A is —C; R₂ and R₃ are both hydrogen; m is 1 or 2 and n is 1.

3. The compound according to claim 1, selected from the group consisting of:

3'-Desamino-(3'S)-N-pyrrolidinyl-11-deoxy-11-[carboxy-(3,4-dichlorophenethylamino)]-6-O-methyl-erythromycin A 11,12-(cyclic carbamate);

3'-Desamino-3'-N-pyrrolidinyl-11-deoxy-11-[carboxy-(3-chloro-4-fluorophenethylamino)]-6-O-methyl-erythromycin A 11,12-(cyclic carbamate);

3'-Desamino-3'-N-piperidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3-chloro-4-fluorophenethylamino)]-6-O-methyl-erythromycin A 11,12-(cyclic carbamate);

3'-Desamino-3'S-N-(2,5-dimethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-dimethylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,6-dimethylpiperidinyl)-11-deoxy-11-[carboxy-(3,4-dichlorophenethylamino)]-6-O-methyl-erythromycin A 11,12-(cyclic carbamate);

3'-Desamino-3'-N-(2,6-dimethylpiperidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate); and 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diallylpyrrolidinyl)-11-deoxy-11-[carboxy-(3,4-dichlorophenethylamnino)]-6-O-methyl-erythromycin A 11,12-(cyclic carbamate);

3'-Desamino-3'-N-(2,5-diallylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-dipropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-dipropylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diisopropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-diisopropylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-biscyclopropylpyrrolidinyl)-11-deoxy-11-[carboxy-(3-chloro-4-fluorophenethylamino)]-6-O-methyl-erythromycin A 11,12-(cyclic carbamate);

3'-Desamino-3'-N-(2,5-biscyclopropylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-biscyclobutylpyrrolidinyl)-11-deoxy-11-[carboxy-(3-chloro-4-fluorophenethylamino)]-6-O-methyl-erythromycin A 11,1 2-(cyclic carbamate);

3'-Desamino-3'-N-(2,5-biscyclobutylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate); and 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate).

4. The compound according to claim 1 selected from the group consisting of:

3'-Desamino-(3'S)-N-pyrrolidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3,4-dichlorophenethylamino)]-6-O-methyl-erythromycin A 11,12-(cyclic carbamate);

3'-Desamino-3'-N-piperidinyl-11-deoxy-11-[carboxy-(3-chloro-4-fluorophenethylamino)]-6-O-methyl-erythromycin A 11,12-(cyclic carbamate);

3'-Desamino-3'S-N-(2,5-dimethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-dimethylpyrrolidinyl)-11-deoxy-11-[carboxy-(3-chloro,4-fluorophenethylamino)]-6-O-methyl-erythromycin A 11,12-(cyclic carbamate);

3'-Desamino-3'-N-(2,6-dimethylpiperidinyl)-11-deoxy-11-[carboxy-(3,4-dichlorophenethylamino)]-6-O-methyl-erythromycin A 11,12-(cyclic carbamate);

3'-Desamino-3'-N-(2,6-dimethylpiperidinyl)-11-deoxy-11-[carboxy-(3-chloro, 4-fluorophenethylamino)]-6-O-methyl-erythromycin A 11,12-(cyclic carbamate);

3'-Desamino-3'-N-(2,5-diethylpyrrolidinyl)-11-deoxy-11-[carboxy-(3,4-dichlorophenethylamino)]-6-O-methyl-erythromycin A 11,12-(cyclic carbamate);

3'-Desamino-3'-N-(2,5-diethylpyrrolidinyl)-11-deoxy-11-[carboxy-(3-chloro-4-fluorophenethylamino)]-6-O-methyl-erythromycin A 11,12-(cyclic carbamate); and 3'-Desamino-3'-N-(2,6-biscyclopropylpiperidinyl)-11-deoxy-11-[carboxy-(3-chloro-4-fluorophenethylamino)]-6-O-methyl-erythromycin A 11,12-(cyclic carbamate).

5. A process of preparing a compound of formula:

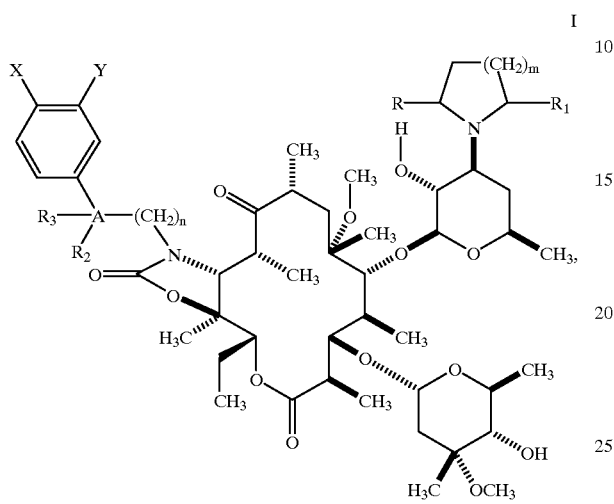

or a pharmaceutically acceptable salt or ester thereof, wherein

A is selected from the group consisting of:
  (a) —C,
  (b) —N, and
  (c) —O;
X and Y are independently at each occurrence selected from the group consisting of:
  (a) hydrogen,
  (b) halide,
  (c) alkoxy,
  (d) alkyl,
  (e) aryl, and
  (f) substituted aryl;
R and $R_1$ are independently at each occurrence selected from the group consisting of:
  (a) alkyl,
  (b) cycloalkyl,
  (c) heterocylic,
  (d) substituted heterocyclic,
  (e) alkylcycloalkyl,
  (f) substituted alkylcycloalkyl,
  (g) alkylaryl,
  (f) alkylheterocyclic,
  (g) alkenyl, and
  (h) alkynyl,
m is 1, 2 or 3
$R_2$ and $R_3$ are independently at each occurrence
  (a) hydrogen,
  (b) methyl, or $R_2$ and $R_3$ together form a cycloalkyl moiety, when A is C; and n=1, 2 or 3; comprising the steps of:
  (a) reacting a compound of formula:

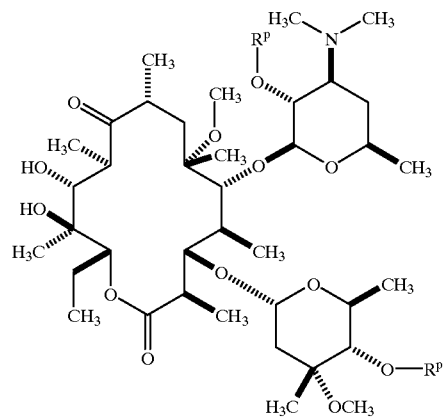

with sodium hexamethyldisilazide and carbonyldiimidazole to afford a compound of the formula:

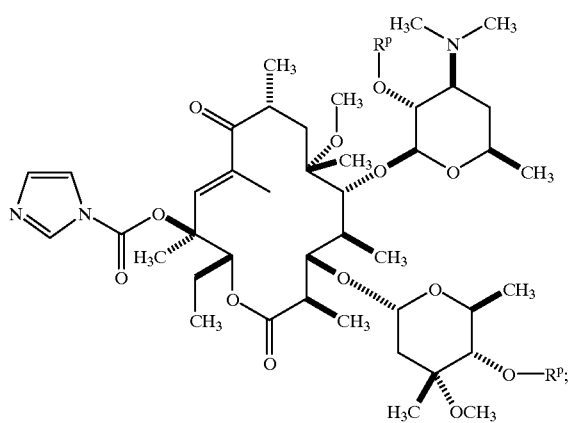

(b) reacting the compound obtained in step (a) with an amino compound of the formula:

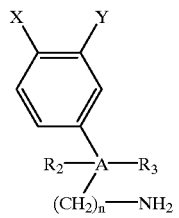

and deprotection to afford a compound of the formula:

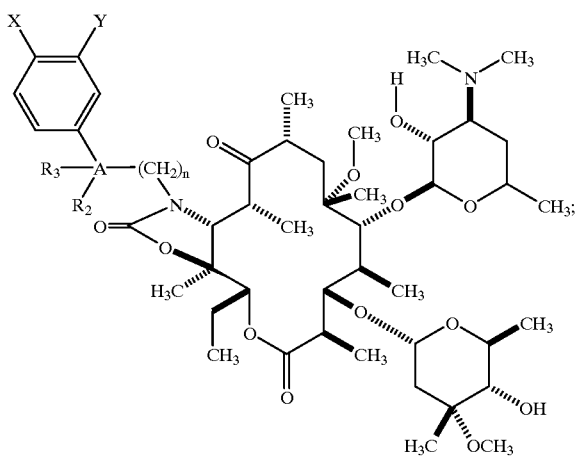

(c) stepwise bisdesmethylating the 3'-amino by treating the compound obtained in step (b) twice with iodine in presence of a base to afford a compound of the formula:

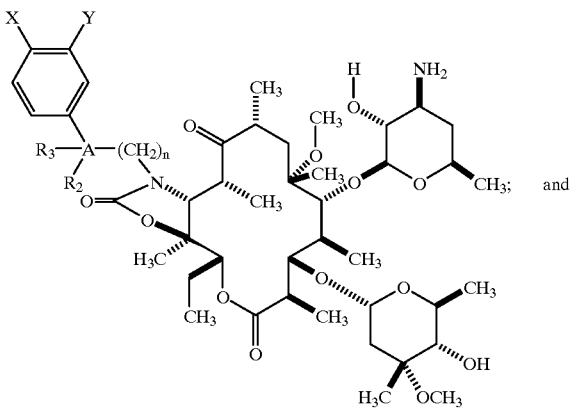

and (d) alkylating the 3',3'-N-bisdesmethylated compound obtained in step (c) with an alkylating agent.

6. The process according to claim 5, wherein the reaction in step (a) is carried out in an aprotic solvent at 0 to 25° C.

7. The process according to claim 5, wherein the reaction in step (b) is carried out without solvent or in acetonitrile at 25 to 80° C.

8. The process according to claim 5, wherein the desmethylation is carried out by reaction of the compound obtained in step (b) with iodine in the presence of a base and a light or heat source.

9. The process according to claim 8, wherein the desmethylation is carried out by reaction of the compound obtained in step (b) with a chloroformate selected from the group consisting of benzyl chloroformate, allyl chloroformate and vinyl chloroformate.

10. The process according to claim 5, wherein the alkylation in step (d) is achieved by reaction of the compound obtained in step (c) with an aldehyde or ketone in the presence of a hydride metal or in the presence of Pd/C catalyst in a protic or non-protic solvent under hydrogen.

11. The process according to claim 5, wherein the alkylation in step (d) is achieved by reaction of the compound obtained in step (c) with an alkyl halide in presence of a base.

12. A pharmaceutical composition for inhibiting the release of LH comprising a therapeutically effective amount of a compound according to claim 1 in combination with a pharmaceutically acceptable carrier.

13. A method of inhibiting LH release and suppressing reproductive hormones in a mammal in need of such treatment comprising administering to the mammal a therapeutically-effective amount of a compound according to claim 1.

* * * * *